(12) United States Patent
Reiley et al.

(10) Patent No.: US 6,974,478 B2
(45) Date of Patent: Dec. 13, 2005

(54) PROSTHESES, SYSTEMS AND METHODS FOR REPLACEMENT OF NATURAL FACET JOINTS WITH ARTIFICIAL FACET JOINT SURFACES

(75) Inventors: Mark A. Reiley, Piedmont, CA (US); Robert M. Scribner, Niwot, CO (US); James Davidson, Irvine, CA (US)

(73) Assignee: Archus Orthopedics, Inc., Redmond, WA (US)

( * ) Notice: Subject to any disclaimer, the term of this patent is extended or adjusted under 35 U.S.C. 154(b) by 74 days.

(21) Appl. No.: 10/158,563

(22) Filed: May 30, 2002

(65) Prior Publication Data

US 2003/0028250 A1 Feb. 6, 2003

Related U.S. Application Data

(63) Continuation-in-part of application No. 10/067,137, filed on Feb. 4, 2002, now Pat. No. 6,811,567, which is a continuation-in-part of application No. 09/693,272, filed on Oct. 20, 2000, now Pat. No. 6,610,091.

(60) Provisional application No. 60/160,891, filed on Oct. 22, 1999.

(51) Int. Cl.[7] .......................... A61F 2/44; A61B 17/56
(52) U.S. Cl. ...................... 623/17.11; 606/61
(58) Field of Search .................. 623/17.11–17.16; 606/60, 70–73, 75

(56) References Cited

U.S. PATENT DOCUMENTS

| | | |
|---|---|---|
| 3,867,728 A | 2/1975 | Stubstad et al. |
| 3,875,595 A | 4/1975 | Froning |
| 4,349,921 A | 9/1982 | Kuntz |
| 4,759,769 A | 7/1988 | Hedman et al. |
| 4,772,287 A | 9/1988 | Ray et al. |
| 4,863,477 A | 9/1989 | Monson |
| 4,904,260 A | 2/1990 | Ray et al. |
| 4,911,718 A | 3/1990 | Lee et al. |
| 5,015,255 A | 5/1991 | Kuslich |
| 5,047,055 A | 9/1991 | Bao et al. |
| 5,062,845 A | 11/1991 | Kuslich et al. |
| 5,071,437 A | 12/1991 | Steffee |
| 5,092,866 A | 3/1992 | Breard et al. |
| 5,147,404 A | 9/1992 | Downey |
| 5,171,280 A | 12/1992 | Baumgartner |
| 5,192,326 A | 3/1993 | Bao et al. |
| 5,258,031 A | 11/1993 | Salib et al. |

(Continued)

FOREIGN PATENT DOCUMENTS

DE 10135771 A1 2/2003

(Continued)

OTHER PUBLICATIONS

Goh, JC et al., "Influence of PLIF cage size on lumbar spine stability", *Spine*, (Jan. 2000), 25(1) Medline abstract (one page).

(Continued)

*Primary Examiner*—David J. Isabella
(74) *Attorney, Agent, or Firm*—Wilson Sonini Goodrich & Rosati; James R. Shay

(57) ABSTRACT

Cephalad and caudal vertebral facet joint prostheses and methods of use are provided. The prostheses provide an artificial facet joint structure including an artificial articular configuration unlike the preexisting articular configuration. The radii and material stress values of the prostheses are configured to sustain contact stress. The cephalad prosthesis provides for posterior-anterior adjustment. Both prostheses permit lateral adjustment and adjustment to accomodate interpedicle distance. Further, the prostheses may be customized to provide a pre-defined lordotic angle and a pre-defined pedicle entry angle.

55 Claims, 19 Drawing Sheets

U.S. PATENT DOCUMENTS

| | | |
|---|---|---|
| 5,300,073 A | 4/1994 | Ray et al. |
| 5,306,308 A | 4/1994 | Gross et al. |
| 5,306,309 A | 4/1994 | Wagner et al. |
| 5,370,697 A | 12/1994 | Baumgartner |
| 5,401,269 A | 3/1995 | Buttner-Janz et al. |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,491,882 A | 2/1996 | Walston et al. |
| 5,507,823 A | 4/1996 | Walston et al. |
| 5,514,180 A | 5/1996 | Heggeness et al. |
| 5,527,312 A | 6/1996 | Ray |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,571,189 A | 11/1996 | Kuslich |
| 5,571,191 A | 11/1996 | Fitz |
| 5,577,995 A | 11/1996 | Walker et al. |
| 5,603,713 A | 2/1997 | Aust et al. |
| 5,645,597 A | 7/1997 | Krapiva |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,702,450 A | 12/1997 | Bisserie |
| 5,716,415 A | 2/1998 | Steffee |
| 5,741,261 A | 4/1998 | Moskovitz et al. |
| 5,824,093 A | 10/1998 | Ray et al. |
| 5,824,094 A | 10/1998 | Serhan et al. |
| 5,836,948 A | 11/1998 | Zucherman et al. |
| 5,860,977 A | 1/1999 | Zucherman et al. |
| 5,865,846 A | 2/1999 | Bryan et al. |
| 5,868,745 A | 2/1999 | Alleyne |
| 5,879,396 A | 3/1999 | Walston et al. |
| 5,893,889 A | 4/1999 | Harrington |
| RE36,221 E | 6/1999 | Breard et al. |
| 6,001,130 A | 12/1999 | Bryan et al. |
| 6,014,588 A | 1/2000 | Fitz |
| 6,019,792 A | 2/2000 | Cauthen |
| 6,039,763 A | 3/2000 | Shelokov |
| 6,048,342 A | 4/2000 | Zucherman et al. |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,113,637 A | 9/2000 | Gill et al. |
| 6,132,464 A | 10/2000 | Martin |
| 6,132,465 A | 10/2000 | Ray et al. |
| 6,200,322 B1 | 3/2001 | Branch et al. |
| 6,293,949 B1 | 9/2001 | Justis et al. |
| 6,419,703 B1 | 7/2002 | Fallin et al. |
| 6,565,605 B2 | 5/2003 | Goble et al. |
| 6,579,319 B2 | 6/2003 | Goble et al. |
| 6,610,091 B1 | 8/2003 | Reiley |
| 6,669,729 B2 | 12/2003 | Chin |
| 6,761,720 B1 | 7/2004 | Senegas |
| 6,764,689 B1 * | 7/2004 | Knuth et al. ............. 424/278.1 |
| 6,783,527 B2 | 8/2004 | Drewry et al. |
| 2001/0012938 A1 | 8/2001 | Zucherman et al. |
| 2001/0020170 A1 | 9/2001 | Zucherman et al. |
| 2002/0029039 A1 | 3/2002 | Zucherman et al. |
| 2002/0151895 A1 | 10/2002 | Soboleski et al. |
| 2004/0116927 A1 | 6/2004 | Graf |
| 2004/0143264 A1 | 7/2004 | McAfee |

FOREIGN PATENT DOCUMENTS

| | | |
|---|---|---|
| IE | S970323 | 6/1998 |
| JP | 10179622 A2 | 7/1998 |
| WO | WO 95/05783 A1 | 3/1995 |
| WO | WO 98/48717 A1 | 11/1998 |
| WO | WO 98/56301 A1 | 12/1998 |
| WO | WO 99/05995 A1 | 2/1999 |
| WO | WO 99/23963 A1 | 5/1999 |
| WO | WO 99/60957 A1 | 12/1999 |
| WO | WO 99/65412 A1 | 12/1999 |
| WO | WO 00/38582 A1 | 7/2000 |
| WO | WO 00/62684 A1 | 10/2000 |
| WO | WO 01/30248 A1 | 5/2001 |
| WO | WO 01/97721 A2 | 12/2001 |
| WO | WO 02/089712 A1 | 11/2002 |
| WO | WO 03/020143 A1 | 3/2003 |

OTHER PUBLICATIONS

Head, WC, "Wagner surface replacement arthroplasty of the hip. Analysis of fourteen failures in forty-one hips", *J Bone Joint Surg. Am.*, (Mar. 1981) 63(3), Medline abstract (one page).

Khoo, LT et al., "A biomechanical analysis of the effects of lumbar fusion on the adjacent vertebral motion segment", Proceedings of the 2000 Annual Meeting of the North American Spine Society, New Orleans.

Kotani, Y. et al., "The effects of spinal fixation and destabilization on the biomechanical and histologic properties of spinal ligaments. An in vivo study.", *Spine*, (Mar. 15, 1998) 23(6), Medline abstract (2 pages).

Lemaire, JP et al., "Intervertebral disc prosthesis: results and prospects for the year 2000", *Clinical Orthopaedics and Related Research*, No. 337, pp. 64-76.

Nagata, H. et al., "The effects of immobilization of long segments of the spine on the adjacent and distal facet force and lumbrosacral motion", *Spine*, (Dec. 1993), 18(16):2471-2479, (9 pages).

Nibu, K. et al., "Multidirectional stabilizing potential of BAK interbody spinal fusion system for anterior surgery [see comments]", *J Spinal Discord*, (Aug. 1997), 10(4), Medline abstract (one page).

Tsantrizos, A. et al., "Segmental stability and compressive strength of posterior lumbar interbody fusion implants", *Spine*, (Aug. 1, 2000) 25(15), Medline abstract (one page).

* cited by examiner

PROSTHESES, SYSTEMS AND METHODS FOR REPLACEMENT OF NATURAL FACET JOINTS WITH ARTIFICIAL FACET JOINT SURFACES

RELATED APPLICATIONS

This application is a continuation-in-part of U.S. patent application Ser. No. 10/067,137, filed Feb. 4, 2002, now U.S. Pat. No. 6,811,567, and entitled "Facet Arthroplasty Devices and Methods," which is a continuation-in-part of U.S. patent application Ser. No. 09/693,272, filed Oct. 20, 2000, now U.S. Pat. No. 6,610,091, and entitled "Facet Arthroplasty Devices and Methods," which claims the benefit of Provisional Patent Application Ser. No. 60/160,891, filed Oct. 22, 1999, and entitled "Facet Arthroplasty Devices and Methods," all of which are incorporated herein by reference.

FIELD OF THE INVENTION

This invention relates to prostheses for treating various types of spinal pathologies, as well as to methods of treating spinal pathologies.

BACKGROUND OF THE INVENTION

I. Vertebral Anatomy

As FIG. 1 shows, the human spinal column 10 is comprised of a series of thirty-three stacked vertebrae 12 divided into five regions. The cervical region includes seven vertebrae 12, known as C1–C7. The thoracic region includes twelve vertebrae 12, known as T1–T12. The lumbar region contains five vertebrae 12, known as T1–T5. The sacral region is comprised of five vertebrae 12, known as S1–S5. The coccygeal region contains four vertebrae 12, known as Co1–Co4.

FIG. 2 shows a normal human lumbar vertebra 12. Although the lumbar vertebrae 12 vary somewhat according to location, they share many features common to most vertebrae 12. Each vertebra 12 includes a vertebral body 14. Two short bones, the pedicles 16, extend backward from each side of the vertebral body 14 to form a vertebral arch 18.

At the posterior end of each pedicle 16 the vertebral arch 18 flares out into broad plates of bone known as the laminae 20. The laminae 20 fuse with each other to form a spinous process 22. The spinuous process 22 serves for muscle and ligamentous attachment. A smooth transition from the pedicles 16 into the laminae 20 is interrupted by the formation of a series of processes.

Two transverse processes 24 thrust out laterally on each side from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the laminae 20. The superior articular processes 26 are sharp oval plates of bone rising upward on each side from the union of the pedicle 16 with the lamina 20. The inferior processes 28 are oval plates of bone that jut downward on each side.

The superior and inferior articular processes 26 and 28 each have a natural bony structure known as a facet. The superior articular facet 30 faces 30, while the inferior articular facet 31 faces downward. As FIG. 3 shows, when adjacent vertebrae 12 are aligned, the facets 30 and 31, capped with a smooth articular cartilage, interlock to form a facet joint 32, also known as a zygapopysial joint.

The facet joint 32 is composed of a superior half and an inferior half. The superior half is formed by the vertebral level below the joint 32, and the inferior half is formed by the vertebral level above the joint 32. For example, in the L4-L5 facet joint, the superior portion of the joint is formed by bony structure on the L-5 vertebra (e.g., a superior articular surface and supporting bone on the L-5 vertebra), and the inferior portion of the joint is formed by bony structure on the L-4 vertebra (e.g., an inferior articular surface and supporting bone on the L-4 vertebra).

As also shown in FIG. 3, an intervertebral disc 34 between each pair of vertebrae 12 permits gliding movement between vertebrae 12. Thus, the structure and alignment of the vertebrae 12 permit a range of movement of the vertebrae 12 relative to each other.

II. Facet Joint Dysfunction

Back pain, particularly in the "small of the back", or lumbosacral (L4-S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called a "pinched" nerve, or nerve compression or impingement. The result is pain, misaligned anatomy, and a corresponding loss of mobility. Pressure on nerves can also occur without facet joint pathology, e.g., a herniated disc.

One type of conventional treatment of facet joint pathology is spinal stabilization, also known as intervertebral stabilization. Intervertebral stabilization prevents relative motion between the vertebrae. By preventing movement, pain can be reduced. Stabilization can be accomplished by various methods.

One method of stabilization is spinal fusion. Another method of stabilization is fixation of any number of vertebrae to stabilize and prevent movement of the vertebrae.

Another type of conventional treatment is decompressive laminectomy. This procedure involves excision of the laminae to relieve compression of nerves.

These traditional treatments are subject to a variety of limitations and varying success rates. Furthermore, none of the described treatments puts the spine in proper alignment or return the spine to a desired anatomy. In addition, stabilization techniques, by holding the vertebrae in a fixed position, permanently limit a person's mobility.

SUMMARY OF THE INVENTION

There is a need for prostheses, systems, and methods that overcome the problems and disadvantages associated with current strategies and designs in various treatments for spine pathologies.

The invention provides prostheses, systems, and methods designed to replace natural facet joints and/or part of the lamina at virtually all spinal levels including L1-L2, L2-L3, L3-L4, L4-L5, L5-S1, T-11-T12, and T12-L1. The prostheses, systems, and methods can restore a desired anatomy to a spine and give back to an individual a desired range of mobility. The prostheses, systems, and methods also can lessen or alleviate spinal pain by relieving the source nerve compression or impingement.

For the sake of description, the prostheses that embody features of the invention will be called either "cephalad" or "caudal" with relation to the portion of a given natural facet joint they replace. As previously described, a given natural facet joint has a superior half and an inferior half. In anatomical terms, the superior half of the joint is formed by the vertebral level below the joint (which can thus be called the caudal portion of the facet joint, i.e., because it is near the feet). The inferior half of the joint is formed by the vertebral level above the joint (which can thus be called the cephalad portion of the facet joint, i.e., because it is near the head). Thus, a prosthesis that, in use, replaces the caudal portion of a facet joint (i.e., the superior half) will be called a "caudal" prosthesis. Likewise, a prosthesis that, in use, replaces the cephalad portion of a facet joint (i.e., the inferior half) will be called a "cephalad" prosthesis.

One aspect of the invention provides a facet joint prosthesis to replace, on a vertebral body, a caudal portion of a natural facet joint (e.g., a superior articular surface and supporting bone structure on the vertebral body). The caudal prosthesis comprises a component sized to be fixed to the vertebral body, e.g., on or near a pedicle. The caudal prosthesis includes an artificial facet joint structure adapted to replace a caudal portion of the natural facet joint after its removal from the vertebral body. The removal of a caudal portion of the natural facet joint and its total replacement by the artificial facet joint structure of the caudal prosthesis frees the orientation of the prosthesis from anatomic constraints imposed by a preexisting articular configuration of the caudal portion of the natural facet joint. Furthermore, the artificial facet joint structure of the caudal prosthesis can comprise an artificial articular configuration that is unlike the preexisting articular configuration, so that a desired articulation or bony anatomy can be restored.

This aspect of the invention also provides a method of replacing, on a vertebral body, a caudal portion of a natural facet joint. The method removes a caudal portion of the natural facet joint from the vertebral body, and, in its place, fixes a component to the vertebral body that includes an artificial facet joint structure adapted to replace the removed caudal portion of the natural facet joint. The artificial facet joint structure can include an artificial articular configuration unlike the preexisting articular configuration of the removed caudal portion of the natural facet joint.

Another aspect of the invention provides a facet joint prosthesis to replace, on a vertebral body, a cephalad portion of a natural facet joint (e.g., an inferior articular surface and supporting bone structure on the vertebral body). The cephalad prosthesis comprises a component sized to be fixed to the vertebral body, e.g., on or near a pedicle, or on or near a lamina, or on or near a spinous process, or combinations thereof. The cephalad prosthesis includes an artificial facet joint structure adapted to replace a cephalad portion of the natural facet joint after its removal from the vertebral body. As with the removal and total replacement of a caudal portion of the natural facet joint, the removal of a cephalad portion of the natural facet joint and its total replacement by the artificial facet joint structure of the cephalad prosthesis makes possible the orientation of the prosthesis free from anatomic constraints imposed by a preexisting articular configuration of the cephalad portion of the natural facet joint. Furthermore, like the caudal prosthesis, the artificial facet joint structure of the cephalad prosthesis can comprises an artificial articular configuration that is unlike the preexisting articular configuration of the natural facet surface (which is removed), so that a desired articulation or bony anatomy can be totally restored.

This aspect of the invention also provides a method of replacing, on a vertebral body, a cephalad portion of a natural facet joint. The method removes a cephalad portion of the natural facet joint from the vertebral body, and, in its place, fixes a component to the vertebral body that includes an artificial facet joint structure adapted to replace the removed cephalad portion of the natural facet joint. The artificial facet joint structure can include an artificial articular configuration unlike the preexisting articular configuration of the removed cephalad portion of the natural facet joint.

Another aspect of the invention provides a prosthesis assembly and related method for replacing a natural facet joint between adjoining first and second vertebral bodies. The assembly and method utilize a first component sized to be fixed to the first vertebral body, which is superior to the second vertebral body. The first component includes a first artificial facet joint structure adapted to replace a cephalad portion of the natural facet joint on the first vertebral body after removal of the cephalad portion of the natural facet joint from the first vertebral body. The assembly and method also comprise a second component sized to be fixed to the second vertebral body. The second component includes a second artificial facet joint structure adapted to replace the caudad portion of the natural facet joint of the second vertebral body after removal of the caudad portion of the natural facet joint from the second vertebral body. Together, the first and second artificial facet joint structures comprise an artificial facet joint. The removal of both cephalad and caudal portions of a natural facet joint and their total replacement by the artificial facet joint structures of the first and second components allows the artificial facet joint to be installed without anatomic constraints imposed by a preexisting articular configuration of the natural facet joint. Furthermore, the artificial facet joint structures of either the first or second components, or both, can comprise create an artificial articular configuration for the artificial facet joint that is unlike the preexisting articular configuration of the removed natural facet joint, so that a desired articulation or bony anatomy can be completely restored.

Various other aspects of the invention provide caphalad and/or caudal prostheses that readily adapt to or physically change the specific anatomy of an individual. For example, a cephalad prosthesis can be capable of being adjusted in either an anterior or posterior direction relative to a vertebra. As another example, a cephalad prosthesis and/or a caudal prosthesis can provide for lateral (left and right) adjustment, to accommodate or create variances in the distance between the right and left pedicles of a single vertebra. Furthermore, a cephalad prosthesis and/or a caudal prosthesis can provide vertical (up and down) adjustment, to accommodate or create variations in interpedicle distance between adjacent vertebra. Or, as another example, a cephalad prosthesis and a caudal prosthesis can together create a desired lordotic angle between adjacent vertebral bodies, or create a predefined pedicle entry angle for mounting each prosthesis on a given vertebral body. And, as yet another example, the configuration of articulating artificial facet joint structures on cooperating caphalad and caudal prostheses can be matched, taking into account the material(s) from which they are made, to minimize contact stress.

Another aspect of the invention provides an intermediate prosthesis that, together with the cephalad and caudal prostheses, makes possible multiple-level facet joint replacement.

Other features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

I. Vertebral Prostheses

Figure 4:
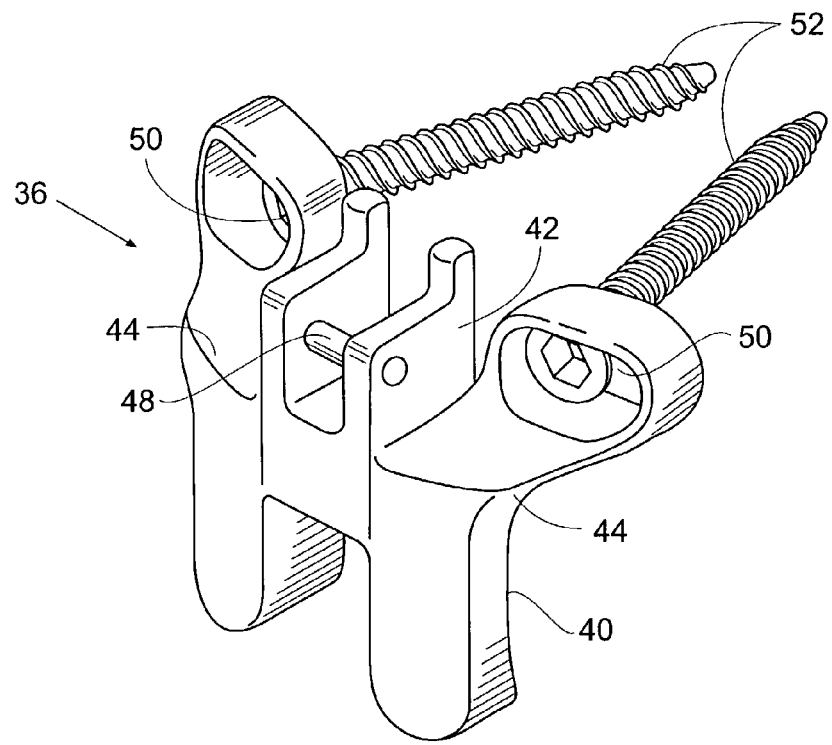
FIG. 4 is a perspective view of a cephalad prosthesis for replacing the inferior half of a natural facet joint.
Figure 5:
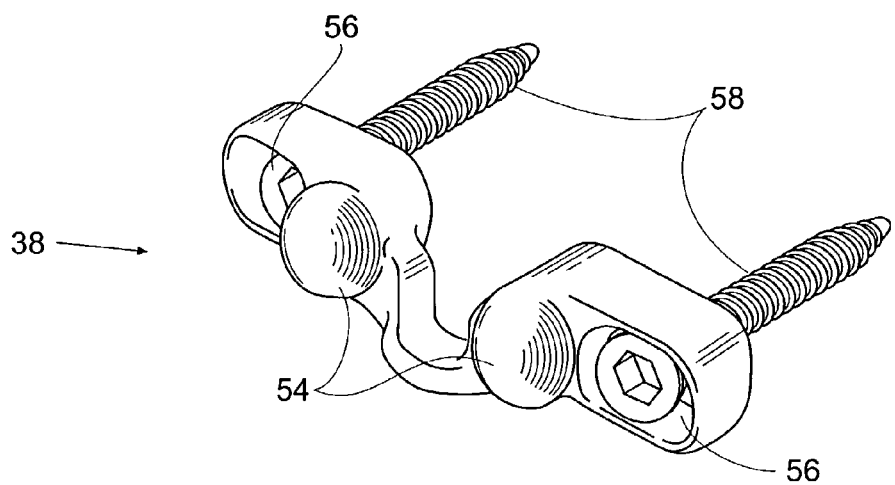
FIG. 5 is a perspective view of a caudal prosthesis for replacing the superior half of a natural facet joint.
Figure 6:
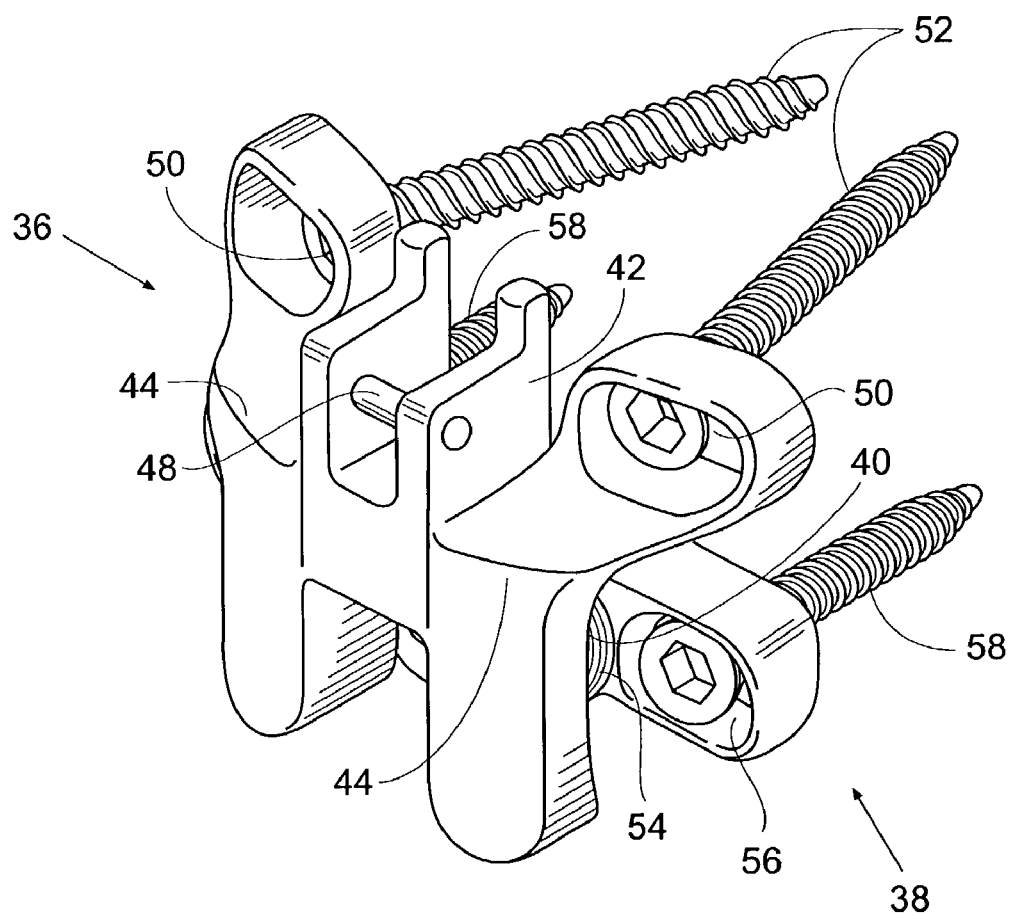
FIG. 6 is a perspective view illustrating the cephalad prosthesis shown in FIG. 4 in articulation with the caudal prosthesis shown in FIG. 5.

FIGS. 4 to 6 illustrate various prostheses for replacing inferior and/or superior portions of natural facet joints. The prostheses are desirably fixed to vertebral bodies following the surgical removal of the respective natural facet joint portions from the vertebral bodies.

FIG. 4 shows a cephalad prosthesis 36 for replacement of the natural inferior half of a facet joint following removal of the natural inferior half of the facet joint. FIG. 5 shows a caudal prosthesis 38 for replacement of the natural superior half of a facet joint following removal of the natural superior half of the facet joint.

Either prosthesis 36 or 38 can be used by itself. The prostheses 36 and 38 each enables bilateral facet joint replacement (both left and right sides of a given vertebral body), or unilateral facet joint replacement (one side of a given vertebral body).

As shown in FIG. 6, the prostheses are desirably used in articulated association between a given pair of vertebral bodies. As FIG. 6 shows, the caudal and cephalad prostheses 36 and 38 form an articulated system that permits total (superior and inferior) facet joint replacement of one or more natural facet joints 32. The system can provide a succession of entirely artificial facet joint structures between two vertebral bodies or along a length of the spinal column 10.

As shown in FIG. 6, the caudal and cephalad prostheses 36 and 38 cooperate in combination to provide an artificial articular configuration. Since the inferior and superior halves of the natural facet joint are removed, the artificial articular configuration need not be constrained by, and can be unlike, the preexisting articulation of the natural facet joint prior to the removal of the inferior and superior halves of the natural facet joint.

A. The Cephalad Prosthesis

The prosthesis 36 shown in FIG. 4 is designated "cephalad" because it provides one or more artificial facet joint structures 40 for the inferior half of a natural facet joint 32. The prosthesis 36 allows for the removal of injured, diseased and/or deteriorating natural inferior articular surfaces 28 and supporting bony structure on the vertebra 12 above the facet joint 32. The artificial structures 40 serve to replace the natural inferior processes 28 and supporting bone of the vertebral body, which have been desirably removed prior to mounting the prosthesis 36 on the vertebral body, as will be described in greater detail later.

The artificial facet joint structures 40 articulate with the superior half of the facet joint 32. The superior half can comprise the natural superior portions of the facet joint 32 (i.e., the natural superior articular surfaces 26 and supporting bony structure on the vertebral body below the facet joint 32). Desirably, however, the superior half comprises an artificial facet joint structure 54 formed by a caudal joint replacement prosthesis 38, shown, e.g., in FIG. 6.

The cephalad prosthesis 36 is sized to extend across the laminae 20 of a vertebral body. In the illustrated embodiment, the caphalad prosthesis comprises a chimney 42 and left and right arm components 44.

The chimney 42 is configured to receive the spinous process 22 of the vertebral body. In this manner, the chimney 42 serves to support and stabilize the prosthesis 36. The chimney 42 desirably includes a lamina hook 46 (best shown in FIG. 7) that rests under the laminae 20 of the vertebral body to further support the prosthesis 36. If desired, the spinous process 22 may be fixed within the chimney 42 with a trans-spinous process screw 48. In some instances, when a significant portion of the laminae 20 is removed, it may be desirable to omit the chimney 42 entirely.

The chimney 42 carries right and left arms 44 in association with the chimney 42. Each arm 44 carries an artificial facet joint structure 40.

As seen in FIGS. 4 and 6, the arms 44 comprise an inferior-to-superior diverging geometry, with a greater lateral width at the superior end than the inferior end, facilitate mounting to the pedicles of a vertebral body. However, other configurations can be used.

Each arm 44 additionally carries at least one opening 50 configured to receive a fixation element 52 for fixing the prosthesis 36 to the vertebral body. It should be understood that the number and location of openings 50 and fixation elements 52 could vary.

In FIG. 4, two openings 40 (right and left) serve to receive two fixation elements 52 (right and left). In the illustrated embodiment, the fixation elements 52 take the form of pedicle screws or nails. The right and left fixation elements 52 are adapted to extend into the right and left pedicles 16 respectively of the vertebral body and serve to anchor the prosthesis 36 in place.

Figure 7:
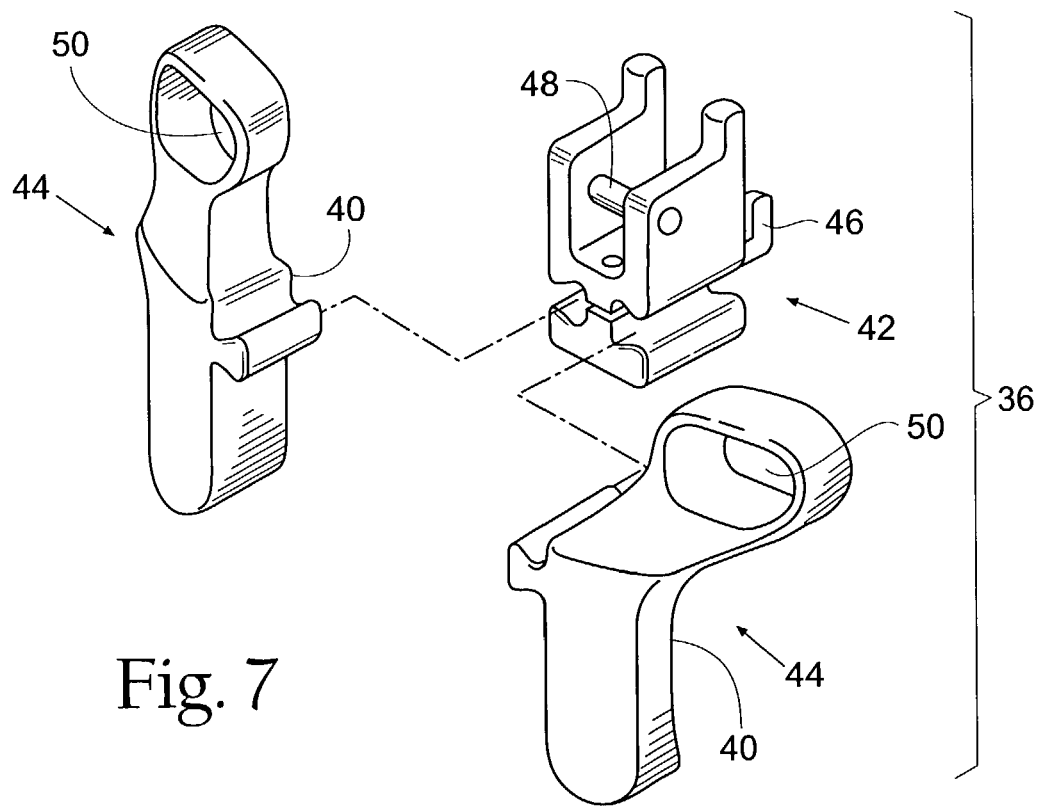
FIG. 7 is an exploded perspective view of an alternative embodiment of a caudal prosthesis for replacing the superior half of a natural facet joint, the prosthesis having a multiple-piece construction.
Figure 8:
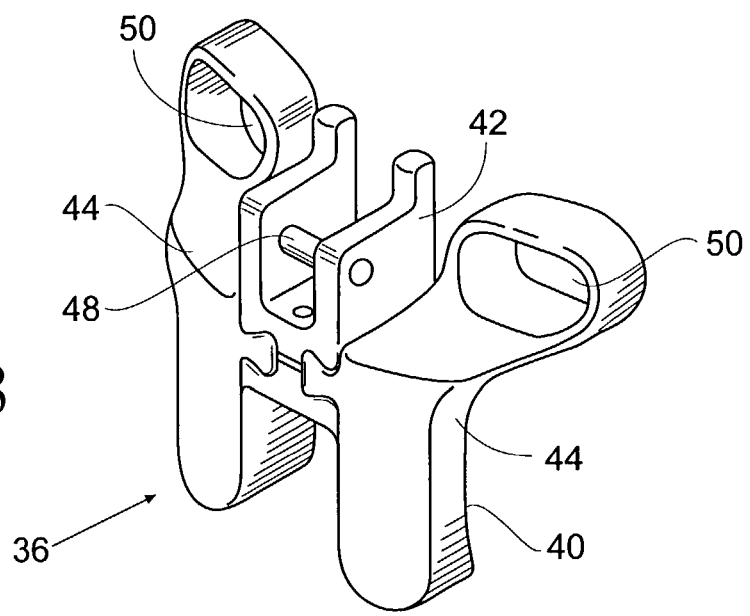
FIG. 8 is an assembled perspective view of the caudal prosthesis shown in FIG. 7.
Figure 9:
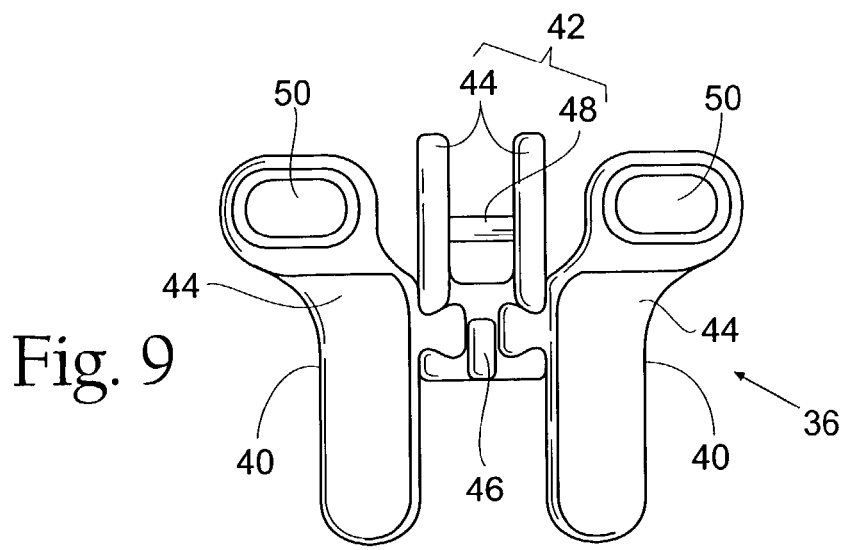
FIG. 9 is a rear view of the caudal prosthesis shown in FIG. 8.

As shown in FIG. 4, the cephalad prosthesis 36 can be of unitary construction, in which the chimney 42 and arms 44 are a single piece. Alternatively, as shown in FIG. 7, the prosthesis 36 can be of multiple-piece construction, in which the arms 44 are configured to be selectively detached from the chimney 42, as will be discussed in greater detail later with respect to FIG. 7.

The cephalad prosthesis 36 may be formed of a material commonly used in the prosthetic arts including, but not limited to, polyethylene, rubber, titanium, chrome cobalt, surgical steel, bony in-growth sintering, sintered glass, artificial bone, ceramics, or a combination thereof.

B. The Caudal Prosthesis

The prosthesis 36 shown in FIG. 5 is designated "caudal" because it creates one or more artificial facet joint structures 54 for the superior half of a natural facet joint. The caudal prosthesis 38 allows for the removal of injured, diseased and/or deteriorating natural superior articular surfaces 32 and supporting bony structure on the vertebral body below the facet joint 32. The artificial structures 54 serve to replace the natural superior processes 26 and supporting bone of the vertebral body, which have been desirably removed prior to mounting the prosthesis 38 on the vertebral body. This aspect will be described in greater detail later.

In use, the artificial facet joint structure 54 articulates with the inferior half of the facet joint 32. The inferior half can comprise the natural inferior portions of the facet joint 32 (i.e., the natural inferior articular surfaces and supporting bony structure on the vertebral body above the facet joint 32). Desirably, however, the inferior half comprises an artificial facet joint structure 40 formed by a cephalad joint replacement prosthesis 36, as FIG. 6 shows.

In the illustrated embodiment, the caudal prosthesis 38 is a bar-like member sized to extend across the laminae 20 of the vertebral body. While FIG. 4 illustrates a unitary construction, the prosthesis 38 can be constructed multiple-parts that are joined together for use.

Like the cephalad prosthesis 36, the caudal prosthesis 38 carries at least one opening 56 configured to receive a fixation element 58 for fixing the prosthesis 38 to the vertebral body and at least one artificial facet joint structure element 54. It is to be understood that the number and location of openings and fixation elements can vary.

In FIG. 5, two openings 56 (right and left) serve to receive two fixation elements 58 (right and left). In the illustrated embodiment, the fixation elements 58 take the form of pedicle screws or nails. The right and left fixation elements 58 are adapted to extend into the right and left pedicles respectively of the vertebral body and serve to anchor the prosthesis 38 in place.

The caudal prosthesis 38 may be formed of a material commonly used in the prosthetic arts including, but not limited to, polyethylene, rubber, titanium, chrome cobalt, surgical steel, bony in-growth sintering, sintered glass, artificial bone, ceramics, or a combination thereof.

II. Additional Features of the Prostheses

Either or both of the cephalad and caudal prostheses 36 and 38 can incorporate a variety of additional features, which adapt the prosthesis 36 or 38 to the specific anatomy encountered or desired. These adaptive features further enhance the restoration of a desired anatomy and/or the alleviated of pain, as will be described in greater detail later. As will become apparent to one skilled in the art, any of the following features can be used alone or in combination with any other feature or features, to "customize" a prosthesis 36 or 38 to a given vertebral location and a specific individual.

A. Posterior-Anterior Adjustment

As shown in FIGS. 7 to 11, the cephalad prosthesis 36 can comprise a multiple-piece construction. The multiple-piece construction permits posterior and anterior (i.e., "front and back") adjustment of the prosthesis 36 relative to the vertebral body. Either symmetric or asymmetric posterior-anterior mounting arrangements are thereby enabled.

In the embodiment shown in FIGS. 7 to 11, the prosthesis 36 is a three-piece assembly comprising a center member 42 (which can comprise the chimney already discussed) and right and left arm components 44. Each arm 44 is a separate piece that is selectively detachable from the center member 42. The arms 44 can be coupled to the center member 42 by a variety of means, including, but not limited to, a slotted joint between the chimney 42 and the respective arm 44, a screw attachment, a hook attachment, or a snap-fit engagement.

Figure 10:
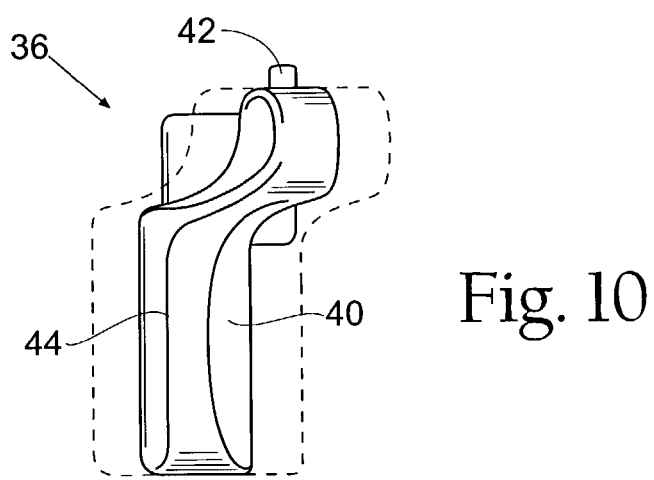
FIG. 10 is a side elevation view of the caudal prosthesis shown in FIG. 8, illustrating, in phantom lines, anterior-posterior adjustment of the arm components.
Figure 11:
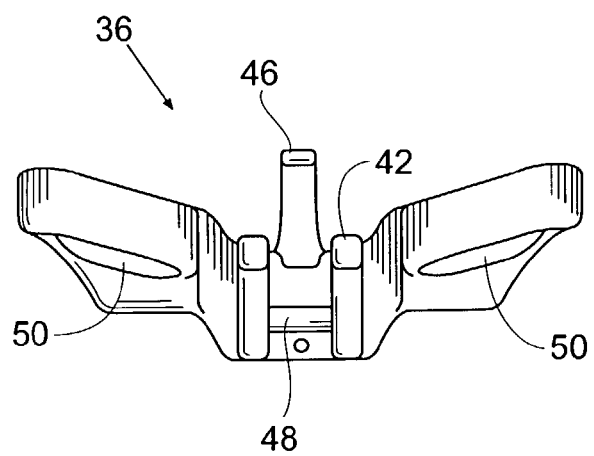
FIG. 11 is a top view of the caudal prosthesis shown in FIG. 8.

A slotted joint or the like allows for relative sliding movement between the respective arm and center member. As best seen in FIG. 10, this arrangement permits independent posterior and anterior adjustment (represented by phantom lines) of the right and left arms 44. The adjustment allows the prosthesis 36 to accommodate the asymmetric anterior-posterior anatomy of a particular vertebral body.

In an alternative construction (not shown), the center member 42 can comprise one piece and the arms 44 are integrally attached to form a second, discrete piece that is selectively attachable and detachable from the member 42. This arrangement would similarly permit posterior and anterior adjustment of the arms 44, but would not permit independent adjustment of the right and left arms 44.

The orientation of the prosthesis 36 is thus not dictated by the natural posterior-anterior anatomy encountered. Instead, the prostheses 36 can be fixed in position between two vertebral bodies in an orientation that corresponds to existing natural anatomy or that establishes a desired posterior-anterior anatomy unlike the natural anatomy.

B. Lateral Adjustment

Figure 12:
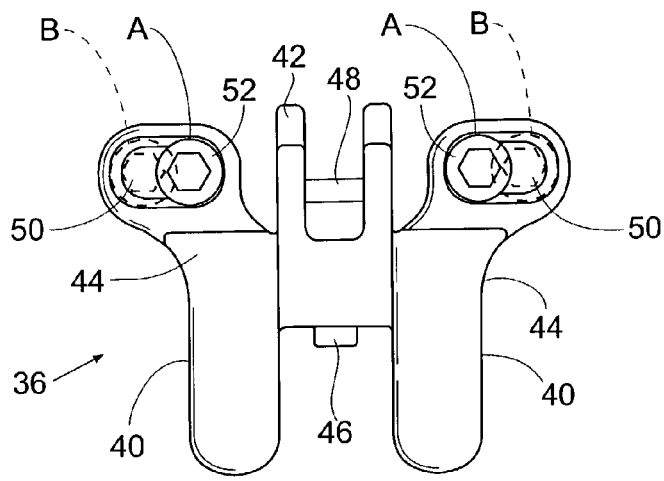
FIG. 12 is a front view of a cephalad prosthesis for replacing the inferior half of a natural facet joint, illustrating horizontally-elongated openings that accommodate lateral adjustment of the prosthesis.
Figure 13:
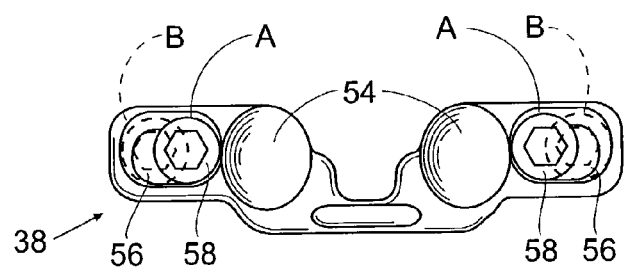
FIG. 13 is a front view of a caudal prosthesis for replacing the superior half of a natural facet joint, illustrating horizontally-elongated openings that accommodate lateral adjustment of the prosthesis.

As seen in FIGS. 12 and 13, any or all of the openings 50 and 56 of the cephalad prosthesis 36 and caudal prosthesis 38 can be horizontally-elongated, i.e., oriented transverse the superior-inferior axis of the prosthesis 36 or 38. The horizontal configuration permits lateral adjustment (i.e., "right to left") of the prosthesis 36 or 38 relative to a vertebral body (see also FIGS. 1–3). Thus, this arrangement allows for variance in distance between the right and left pedicles 16 of a single vertebra 12.

The horizontal configuration allows the fixation elements 52 and 58 on opposite lateral sides of the prostheses 36 and 38 to be placed anywhere between an "A" position (illustrated by solid lines in FIGS. 12 and 13) and a "B" position (illustrated by phantom lines in FIGS. 12 and 13).

The lateral orientation of the artificial facet joint structures of the prostheses 36 or 38 is thus not dictated by the natural lateral anatomy (i.e., intrapedicular distance) encountered. Instead, the position of the artificial facet joint structures of the prostheses 36 and 38 can be changed relative to the position of the pedicles, either medial to or lateral to the pedicles (establishing a desired lateral anatomy unlike the natural anatomy), or in an orientation that corresponds to an existing natural anatomy.

C. Adjustment of Interpedicle Distance

Figure 14:
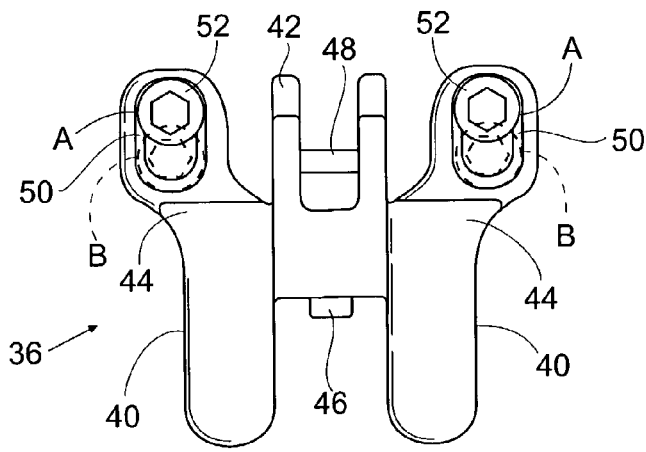
FIG. 14 is a front view of a cephalad prosthesis for replacing the inferior half of a natural facet joint, illustrating vertically-elongated openings that accommodate adjustment of the prosthesis to accommodate varying interpedicle distances.
Figure 15:
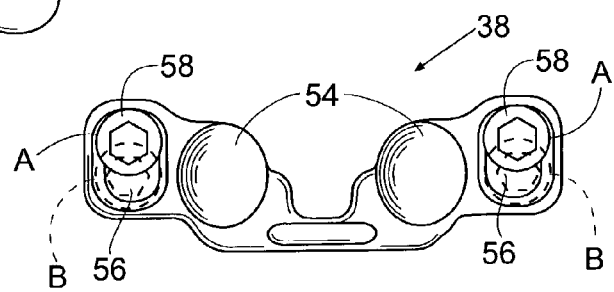
FIG. 15 is a front view of caudal prosthesis for replacing the superior half of a natural facet joint, illustrating vertically-elongated openings that accommodate adjustment of the prosthesis to accommodate varying interpedicle distances.

Referring now to FIGS. 14 and 15, any or all of the openings 50 and 56 of either or both of the cephalad and caudal prostheses 36 and 38 can be vertically-elongated along the superior-inferior axis of the prosthesis 36 or 38. The vertical arrangement permits superior and inferior (i.e., "up and down") adjustment of the prosthesis 36 or 38 relative to a vertebral body (see also FIGS. 1–3).

The vertical configuration allows the fixation elements 52 and 58 to be placed anywhere from an "A" position (illustrated by solid lines in FIGS. 14 and 15) and a "B" position (illustrated by phantom lines in FIGS. 14 and 15). This arrangement permits the distances between the pedicles 16 of adjacent vertebral bodies to be varied. It therefore accommodates asymmetric pedicle 16 orientation (i.e., lateral alignment of the pedicle 16) while maintaining vertical alignment of the prosthesis 36 or 38.

The orientation of the prostheses 36 and 38 is not dictated by the natural interpedicular distances encountered. Instead, the prostheses 36 and 38 can be fixed in position between two vertebral bodies in an orientation that corresponds with the existing natural anatomy or that establishes a desired interpedicular distance unlike the natural preexisting interpedicle distance. The prostheses 36 and 38 thereby serve to create a desired interpedicular distance for the vertebral bodies consistent with a desired anatomy.

D. Lordotic Angle Adjustment

Figure 1:
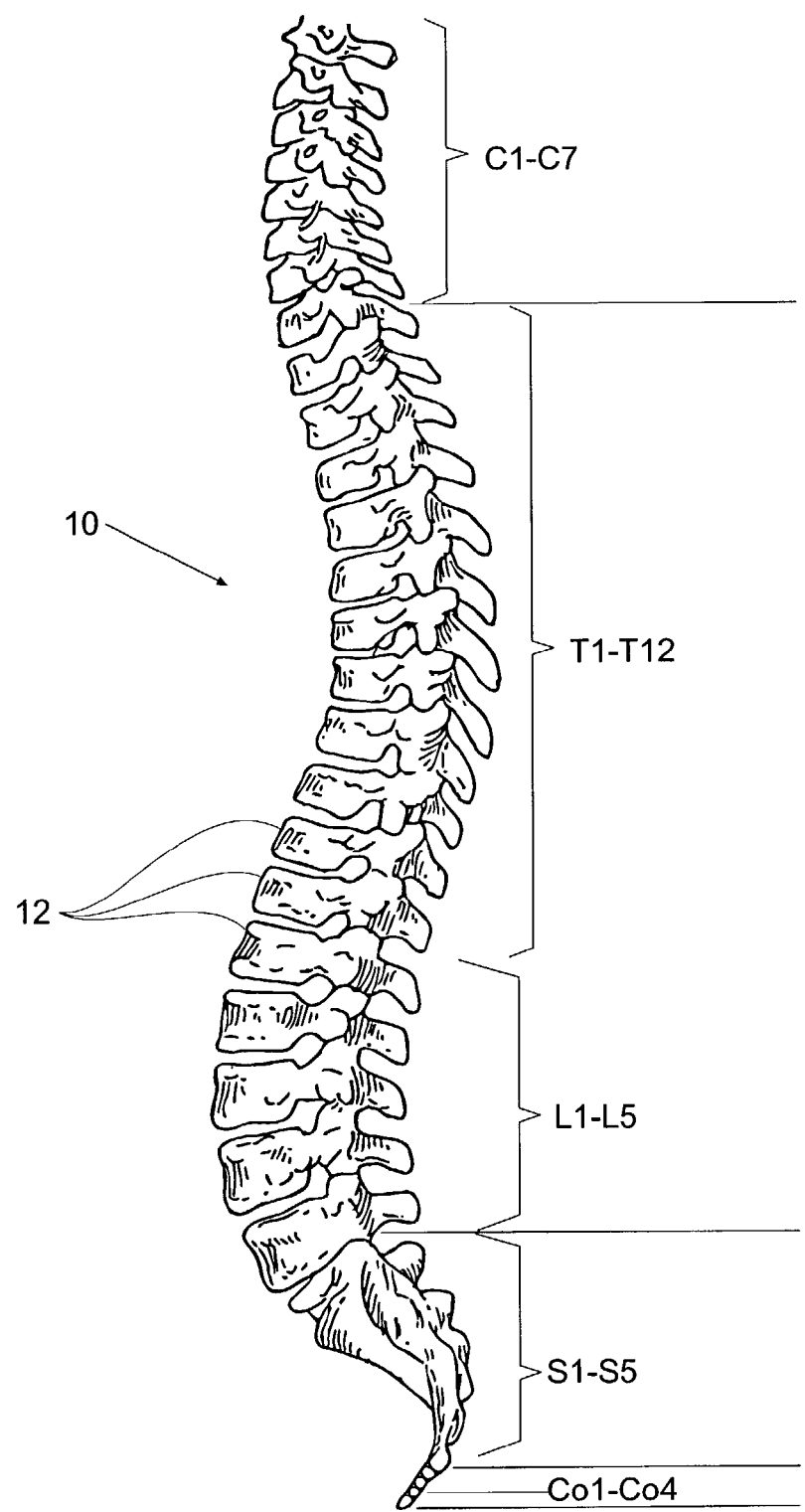
FIG. 1 is a lateral elevation view of a normal human spinal column.

As shown in FIG. 1, the cervical and lumbar regions of the spinal column 10 normally have an anteriorly convex curvature, known as lordosis. The curvature defines a lordotic angle between adjacent vertebral bodies, which is defined by the superior/inferior orientation of the end plates of adjacent vertebral bodies. The lardotic angle varies between adjacent vertebral bodies along the spine. A desired anatomy results by maintaining desired lordotic angles along the spine, which assures desired ligament distention and posture.

In the illustrated embodiment (see FIG. 16), the openings 50 and 56 of adjacent cephalad and caudal prostheses 36 and 38 are mutually oriented in non-parallel planes along the inferior-superior axis. The non-parallel orientation of the planes defines between the fixation elements 52 and 58, when supported by the openings 50 and 56, an angle that results a desired lordotic angle. The mutual orientation and the resulting angle defined depends upon the intended location of the prostheses 36 and 38 along the spinal column 10.

Figure 16:
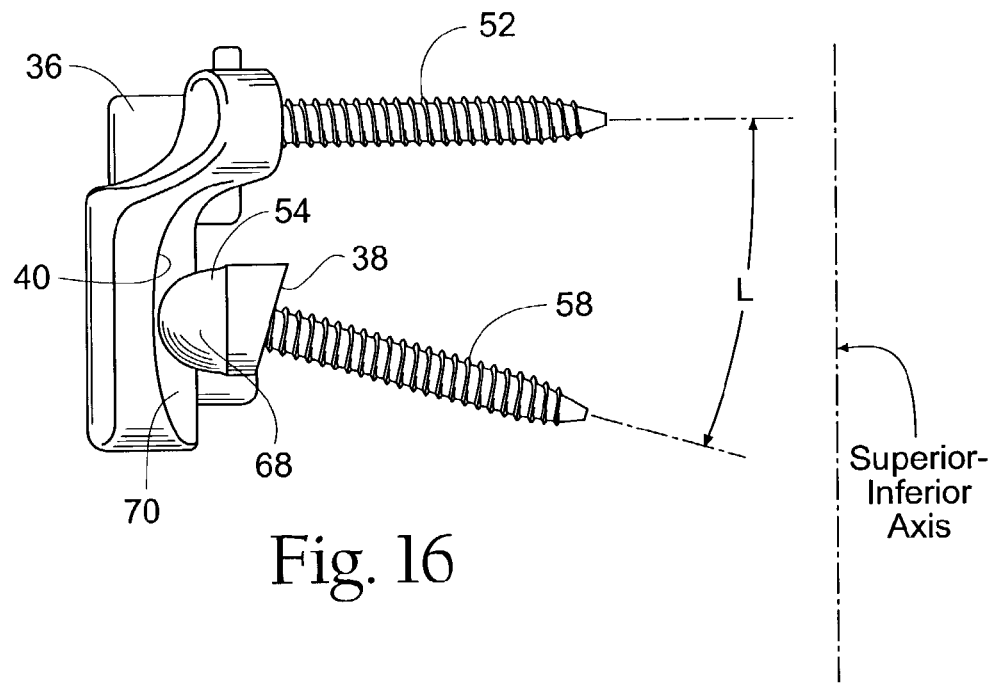
FIG. 16 is a side view of the cephalad prosthesis shown in FIG. 4 in articulation with the caudal prosthesis shown in FIG. 5, illustrating the orientation of the fixation openings relative to a superior-inferior axis to provide a pre-defined lordotic angle.

The defined angle is designated angle "L" in FIG. 16. In FIG. 16, the angle L is defined by orienting the plane of the opening 50 of the cephalad prosthesis 36 generally parallel to the inferior-superior axis, while tilting the plane of the opening 56 of the caudal prosthesis 38 generally downward at an acute inferior angle relative to the inferior-superior axis. The resulting defined angle L between the fixation elements 52 and 58 in FIG. 16 (about 15°) achieves a desired lordotic angle for the L4-L5 level.

The orientation of the prostheses 36 and 38 is not dictated by preexisting natural lordotic angle between two vertebral bodies. Instead, the prostheses 36 and 38 can be fixed in position between two vertebral bodies in an orientation that establishes a desired lordotic angle unlike the natural preexisting angle. The prostheses 36 and 38 thereby serve to create a desired lordotic angle for the vertebral bodies consistent with a desired anatomy.

Changes in the thickness of and/or orientation of the artificial facet joint structures on either or both prostheses 36 and/or 38 can also affect a desired lardotic angle between adjacent vertebral bodies.

E. Adjustment of Pedicle Entry Angle

Figure 2:
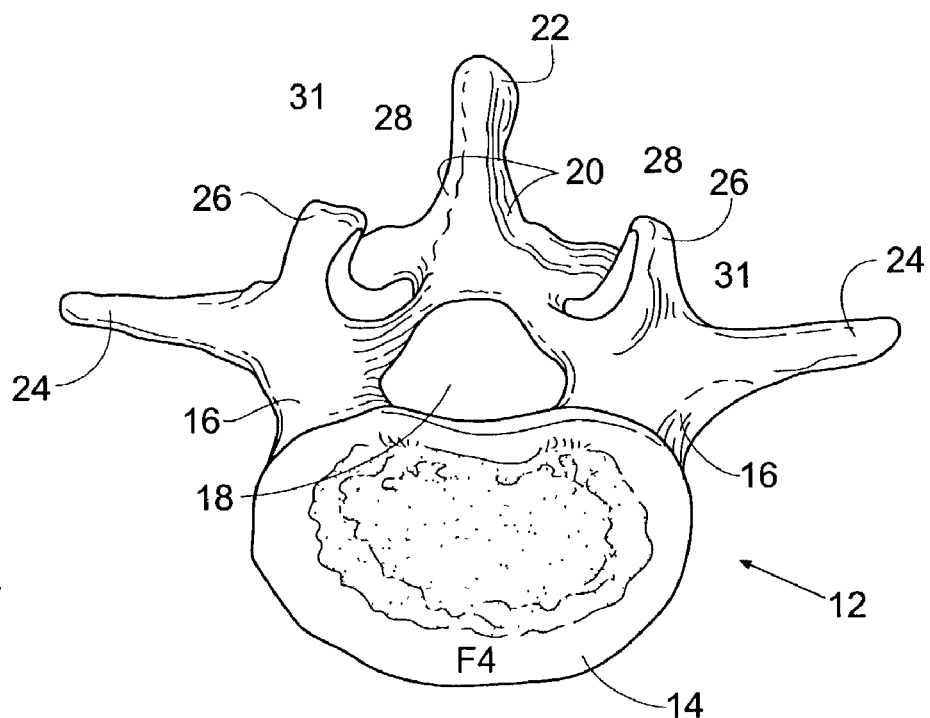
FIG. 2 is a superior view of a normal human lumbar vertebra.
Figure 3:
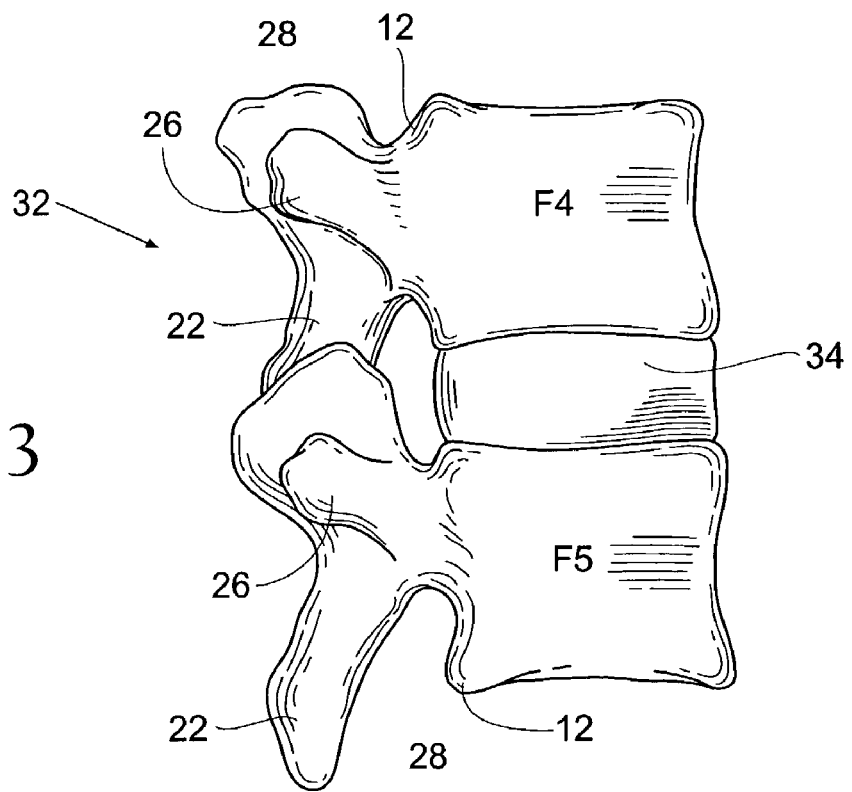
FIG. 3 is a lateral elevation view of a vertebral lumbar facet joint.
Figure 17:
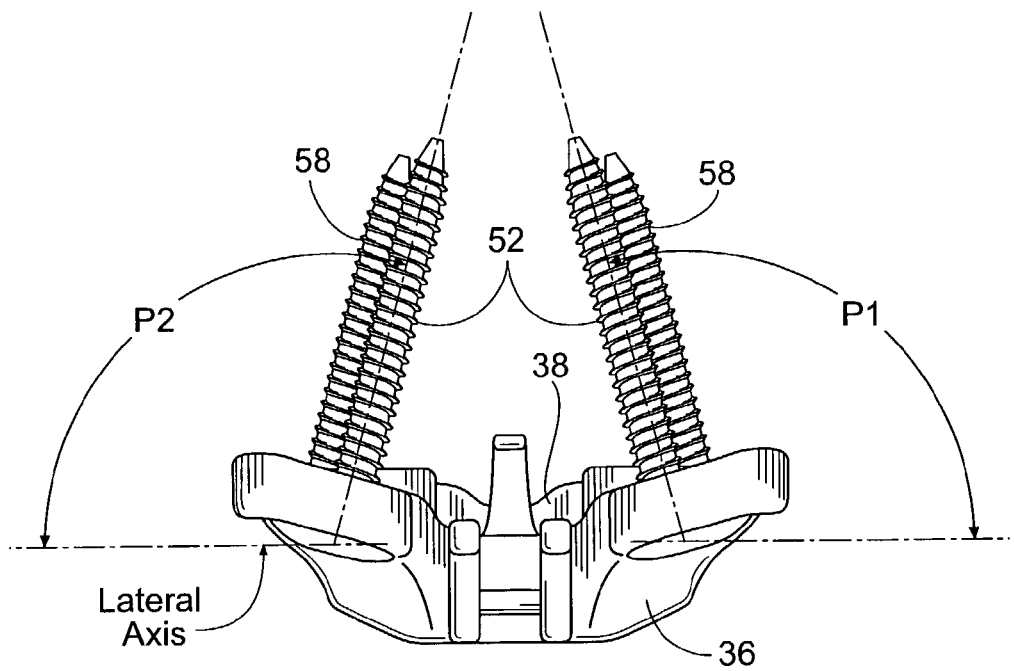
FIG. 17 is a top view of the cephalad prosthesis shown in FIG. 4 in articulation with the caudal prosthesis shown in FIG. 5, illustrating the orientation of the fixation openings relative to a lateral axis to provide a pre-defined pedicle entry angle.

As shown in FIG. 2, the pedicles 16 extend from a vertebral body at an angle. With reference to FIG. 17, to fix the fixation elements 50 and 58 securely within the pedicle 16, it is desirable for the fixation elements 52 and 58 to enter the pedicle 16 at an angle approximating the natural angle of the pedicle 16, e.g., about 15° at the L4 and L5 level.

To achieve the desired angle, the openings 50 and 56 of adjacent cephalad and caudal prostheses 36 and 38 are mutually tilted inwardly to define between a lateral axis and the fixation elements 52 and 58, when supported by the openings 50 and 56, an angle that approximates a desired pedicle entry angle P1/P2. In the illustrated embodiment (FIG. 17), the right fixation element 52 or 58 extends at a first angle (designated "P1" in FIG. 17) and the left fixation element 52 or 58 extends at a second angle (designated "P2" in FIG. 17). In the illustrated embodiment, P1 is generally the same as P2. However, the angles P1 and P2 can differ.

While the illustrated embodiment shows cephalad and caudal prostheses 36 and 38 having the same pedicle entry angles (i.e., P1 and P2 are the same for the cephalad and caudal prostheses 36 and 38), it is to be understood that the cephalad and caudal prostheses 36 and 38 can be formed to have different pedicle entry angles.

F. Multiple-Level Replacement

Figure 18:
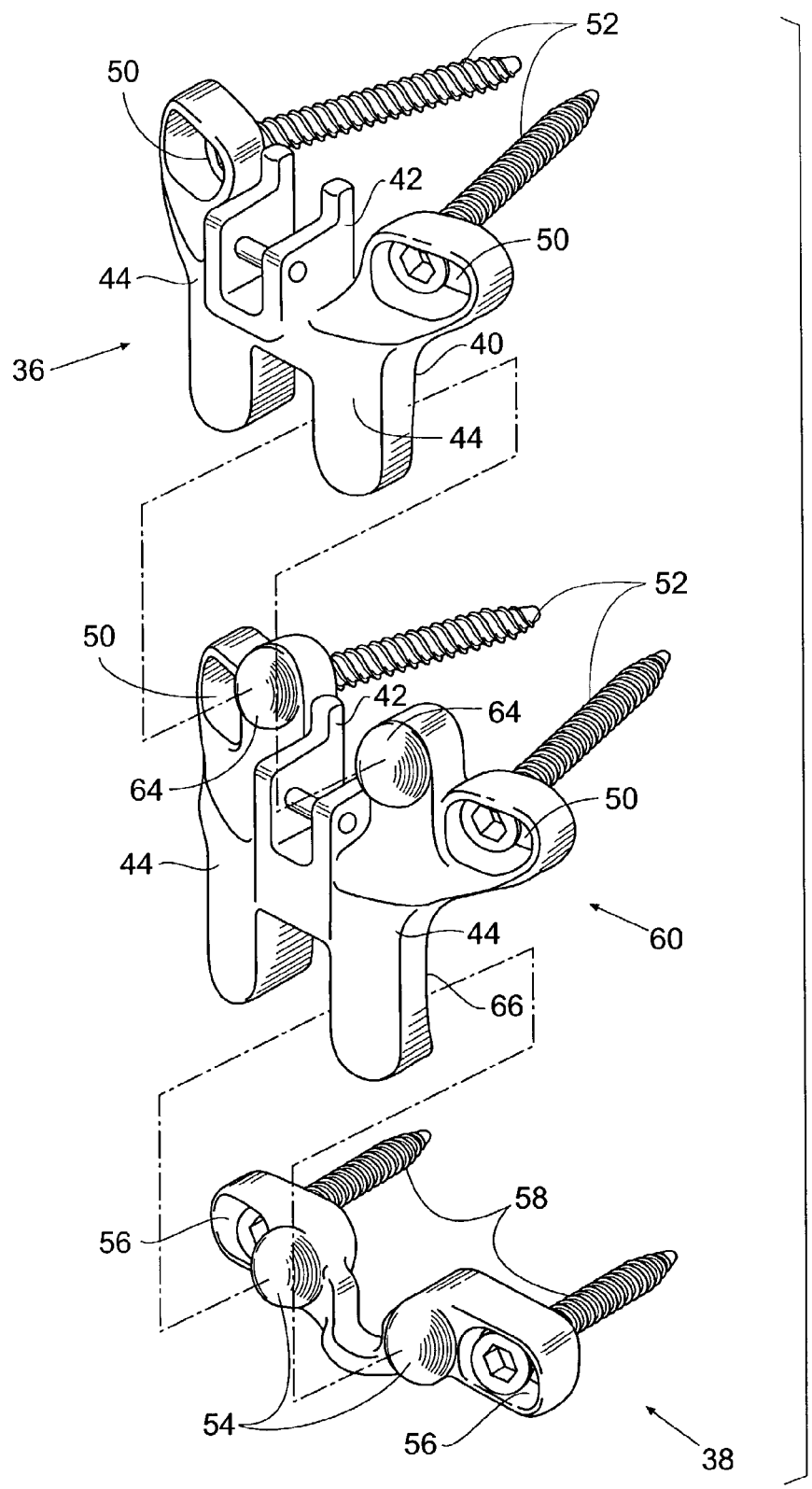
FIG. 18 is an exploded perspective view of a multiple-level prosthesis system comprising a cephalad prosthesis for replacing the inferior halves of natural facet joints on a first superior vertebral body, a caudal prosthesis for replacing the superior halves of natural facet joints on a second inferior vertebral body, an intermediate prosthesis for replacing both inferior and superior halves of natural facet joints on a third vertebral body between the first and second vertebral bodies.
Figure 19:
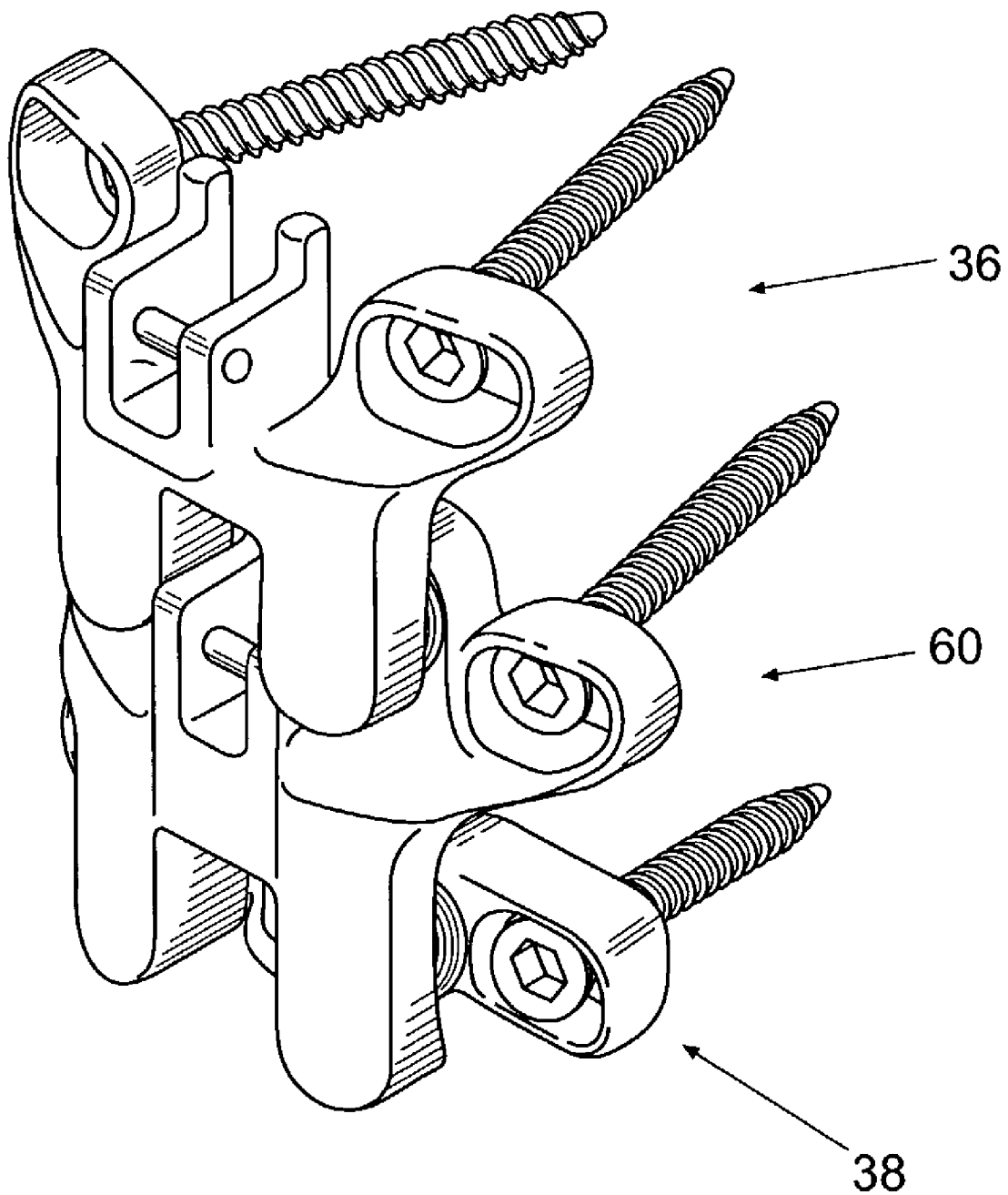
FIG. 19 is an assembled perspective view of the multiple-level prosthesis system shown in FIG. 18.
Figure 20:
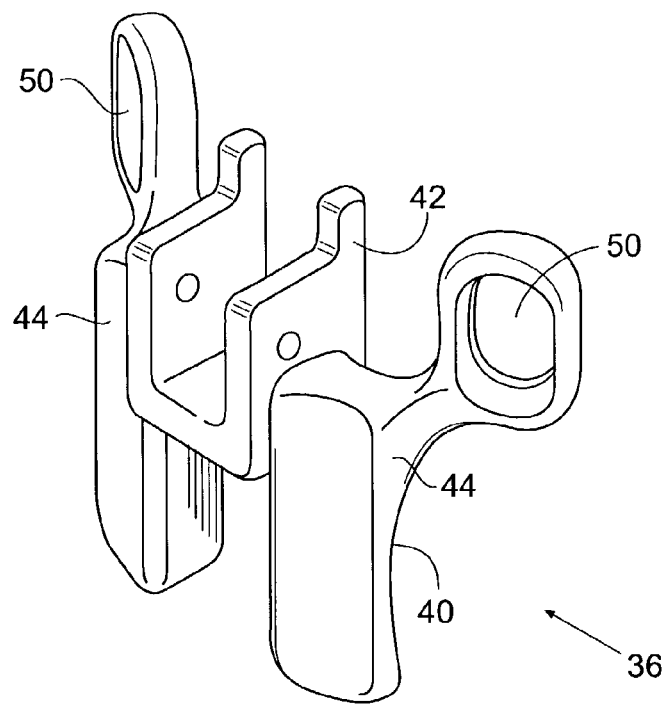
FIG. 20 is a perspective view of a representative embodiment of a cephalad prosthesis for replacing the inferior half of a natural facet joint.
Figure 21:
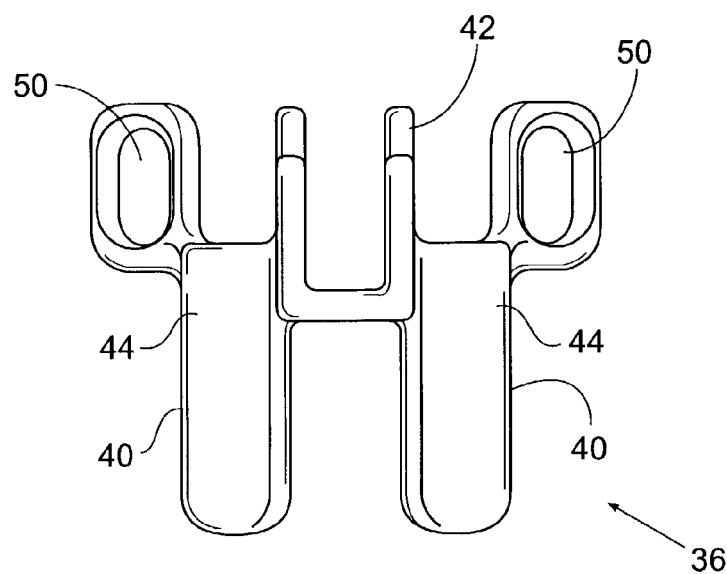
FIG. 21 is a front view of the cephalad prosthesis shown in FIG. 20.

As shown in FIGS. 18 and 19, the cephalad and caudal prostheses 36 and 38 can be coupled by an intermediate prosthesis 60, permitting multiple-level facet joint replacement. The cephalad prosthesis 36 is placed on a most superior vertebral body, e.g., L3. The intermediate prosthesis 60 is placed on the next adjacent inferior vertebral body, e.g., L4. The caudal prosthesis 38 is placed on the next adjacent inferior vertebral body, e.g., L5.

The intermediate prosthesis 60 is similar to the cephalad prosthesis 36 previously described, having a chimney 42 and two openings (right and left) 50 that receive fixation elements 52. Right and left arms 44 provide a first and second pairs of artificial facet joint structures 64 and 66. The first pair 64 is configured to replace the superior processes 26 and related bony structure of the middle vertebral body, and to articulate with the artificial facet joint surfaces 40 of the cephalad prosthesis 36. The second pair 66 is configured to replace the inferior processes 28 and related bony structure of the middle vertebral body, and to articulate with the artificial facet joint surfaces 54 of the caudal prosthesis 38.

G. Ability to Sustain Contact Stress

In the prostheses 36 and 38, each artificial facet joint structure 40/54 creates a bearing surface having a configuration that facilitates articulation with the bearing surface of another artificial facet joint structure. The particular geometry for the bearing surface configuration for a given artificial facet joint structure 40/54 can vary. It can, for example, be concave, convex, or flat. It may also include a hybrid of curved and flat bearing surface designs, i.e., Miniscal, hinge, etc.

The radii of two articulating bearing surface configurations are desirably selected and matched, taking into account the material from which the surfaces are formed, to minimize contact stress during articulation.

For example, in the embodiment illustrated in FIG. 16, the cephalad prosthesis 36 includes artificial facet structures 40 employing generally concave surfaces 68, forming socket-like artificial facet joint structures. In this arrangement, the caudal prosthesis 38 includes artificial facet structures 54 employing generally complementary convex surfaces 70, forming hemisphere-like artificial facet joint structures that articulate with the socket-like artificial facet joint structures. It should be appreciated that the articulating surfaces can be reversed, with the artificial facet structures 40 of the cephalad prosthesis 36 employing generally hemispherical-like surfaces, and the artificial facet structures 54 of the caudal prosthesis 38 employing generally socket-like surfaces.

Alternatively, a Miniscal bearing design could be employed, utilizing a conformal curved surface as one artificial facet joint structure, with the bearing side of the opposed artificial facet joint structure having an essentially flat surface. A hemiarthroplasty design could also alternatively be employed, in which one surface of the opposing surfaces does not incorporate the use of an artificial facet joint structure.

In another arrangement, one surface of an artificial facet joint structure can have bearing articulation on both sides of the component and have opposing articulation with a receiving artificial facet joint structure with having opposing mating bearing surfaces.

A variety of materials are suitable for the artificial facet joint structures. Ceramic or ceramic in opposition with a chrome alloy can be used. Suitable stainless steel, including 3161, or titanium alloys, with or without the use of surface hardening and overlay, or hard surface coatings, including zirconia and alumina, can also be employed. The metal surfaces can be made from cast, wrought, hot-forged, or powder-metal consolidated sintered materials. Any of these metals or combination of metals and ceramics can be used in articulation with each other: Biocompatible polymers, e.g., polyethylene, can also be used in articulation with the metals, ceramic, and surface-hardened metals just described. Ultra High Molecular Weight Polyethylene can further be gamma-irradiated, as-molded or as-machined.

The radii of articulating artificial facet joint structures are desirably closely matched to provide contact stress values less than a given threshold value. The desired contact stress value changes with the material employed.

For example, the contact stress value for metal-to-metal bearing combinations is desirably less than about 25,000 psi, and preferably less than 12,000 psi. For polymer surfaces bearing against a metal, ceramic, or surface-hardened metal counter bearing surface, the contact stress value is desirably less than 10,000 psi, and preferably less than 5,000 psi.

For a given material to achieve a desired contact stress value less than the threshold value, the appropriate radii must be chosen. Thus, the radii chosen will change as material changes.

III. Representative Embodiments

A. Cooperating Caphalad and Caudal Prostheses

FIGS. 20 to 24 show a representative embodiment of a cephalad prosthesis 36 that embody features previously described.

Figure 23:
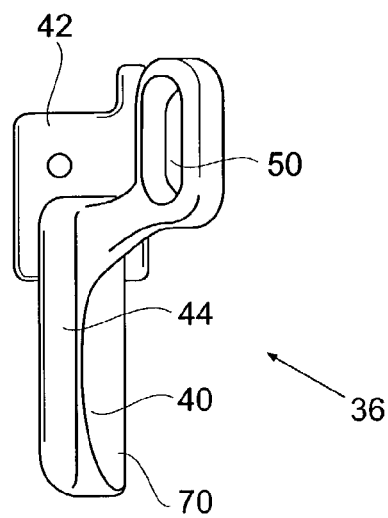
FIG. 23 is a side view of the cephalad prosthesis shown in FIG. 20.

The prosthesis 36 comprises right and left arm components 44 joined to a chimney 42 in a single-piece, unitary construction. Each arm 44 includes an artificial facet joint structure 40 (right and left). As best seen in FIG. 23, each artificial facet joint structure 40 comprises a concave surface 70, forming a socket-like bearing surface.

Figure 22:
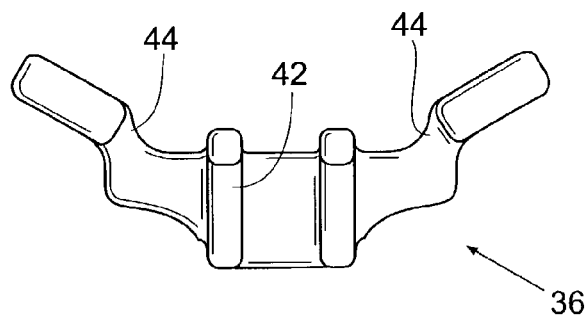
FIG. 22 is a top view of the cephalad prosthesis shown in FIG. 20.

In the illustrated embodiment (see FIG. 24), the fixation openings 50 are vertically-elongated, thereby permitting adjustment of the prosthesis 36 to create a desired interpedicle distance. As best seen in FIG. 22, both the right and left openings 50 are also oriented inward, to provide a pre-defined pedicle entry angle for the fixation elements 52.

Figure 24:
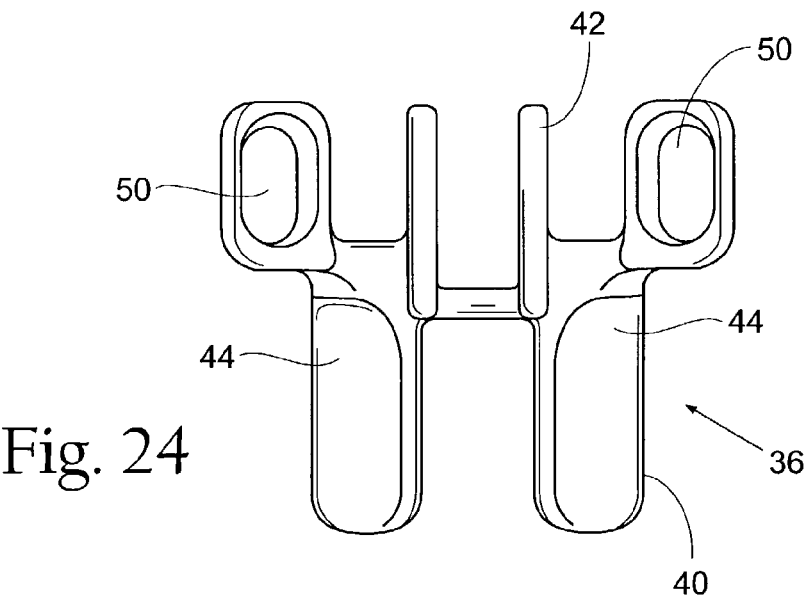
FIG. 24 is a rear view of the cephalad prosthesis shown in FIG. 20.
Figure 25:
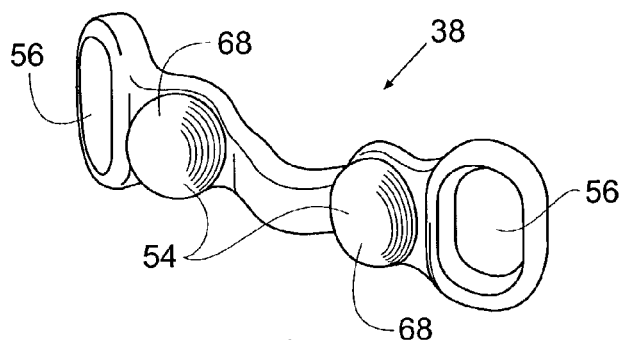
FIG. 25 is a perspective view of a representative embodiment of a caudal prosthesis for replacing the superior half of a natural facet joint.
Figure 26:
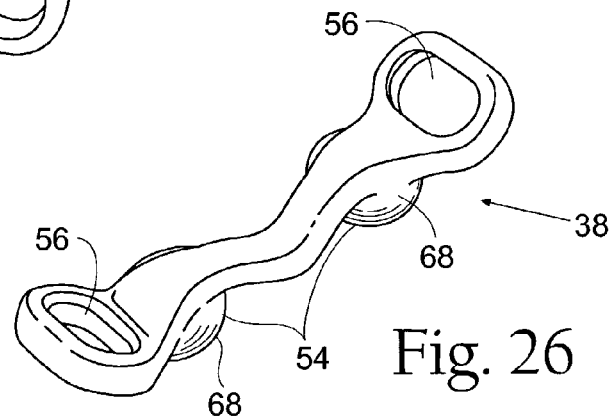
FIG. 26 is a rear view of the caudal prosthesis shown in FIG. 25.
Figure 27:
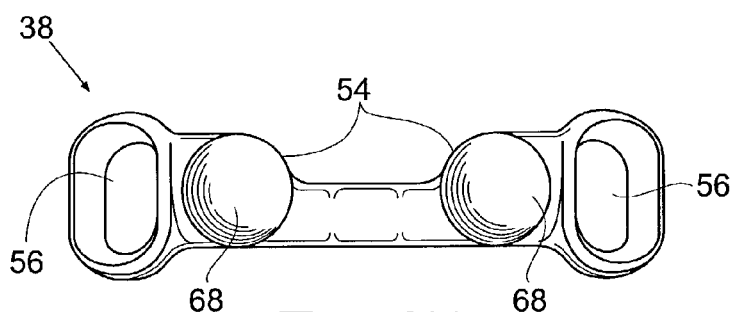
FIG. 27 is a front view of the caudal prosthesis shown in FIG. 25.

FIGS. 25 to 29 show a representative embodiment of a caudal prosthesis 38 that embody features previously described and that is intended to be used in articulation with the cephalad prosthesis 36 shown in FIGS. 22 to 24. FIGS. 31 to 34 show the caudal prosthesis 38 in articulation with the cephalad prosthesis 36.

The prosthesis 38 includes a pair of artificial facet joint structures 54 (right and left). Each artificial facet structure element 54 includes a convex surface 68, forming hemaspherical-like bearing surface. The surfaces 68 are intended, in use, to articulate with the socket-shaped bearing surfaces 40 on the cephalad prosthesis 36 (see FIG. 32).

In the illustrated embodiment, the openings 56 are vertically-elongated, thereby permitting adjustment of the prosthesis 38 to create a desired interpedicle distance. The vertical openings 50 and 56 on the prostheses 36 and 38 permit each prosthesis 36 and 38 to be independently adjusted to create a desired interpedicle distance.

Figure 28:
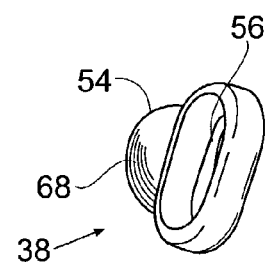
FIG. 28 is a side view of the caudal prosthesis shown in FIG. 25.
Figure 29:
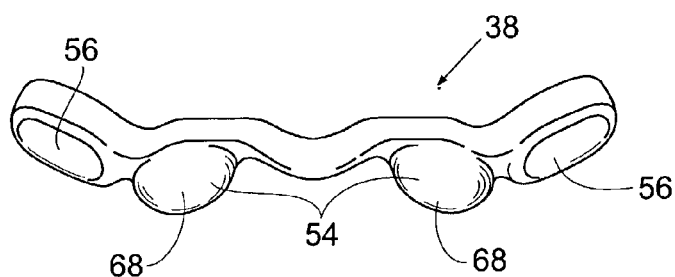
FIG. 29 is a top view of the caudal prosthesis shown in FIG. 25.
Figure 30:
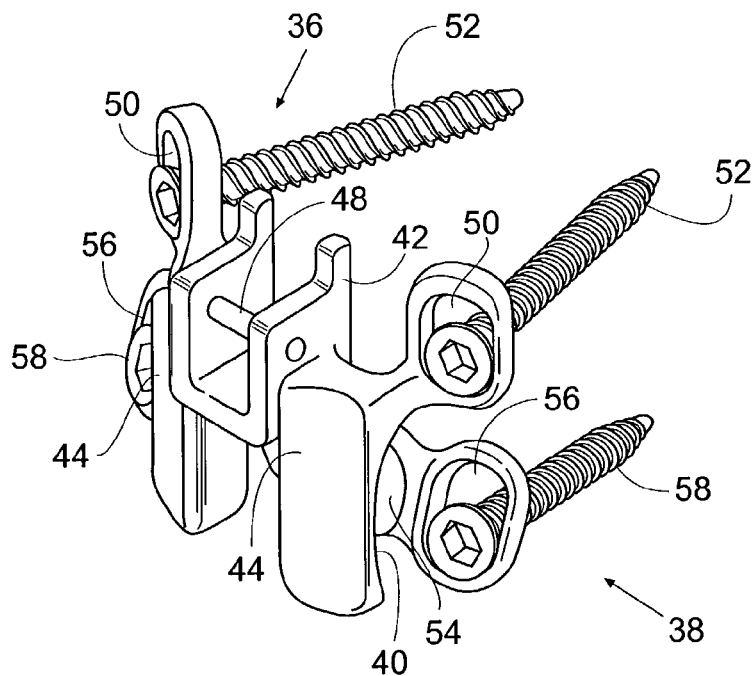
FIG. 30 is a perspective view of the cephalad prosthesis shown in FIG. 20 in articulation with the caudal prosthesis shown in FIG. 25.
Figure 31:
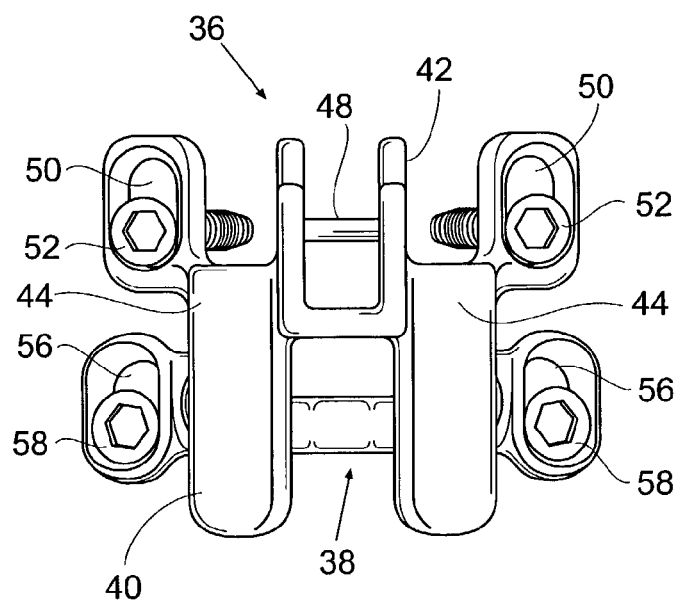
FIG. 31 is a front view of the articulated prostheses shown in FIG. 30.
Figure 32:
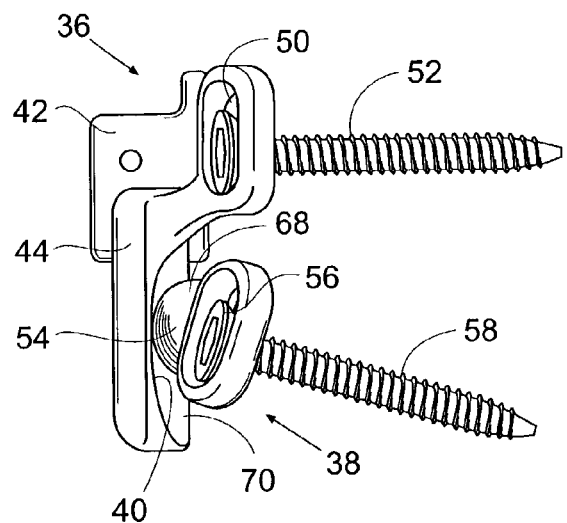
FIG. 32 is a side view of the articulated prostheses shown in FIG. 30.
Figure 33:
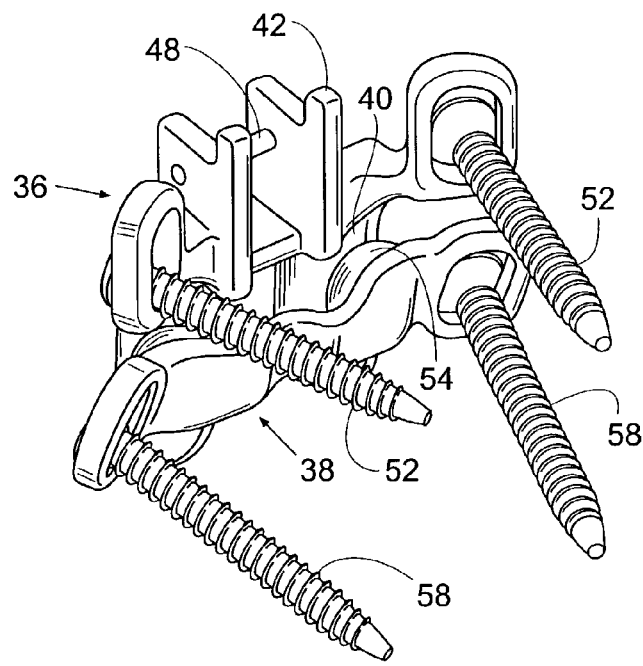
FIG. 33 is a rear view of the articulated prostheses shown in FIG. 30.
Figure 34:
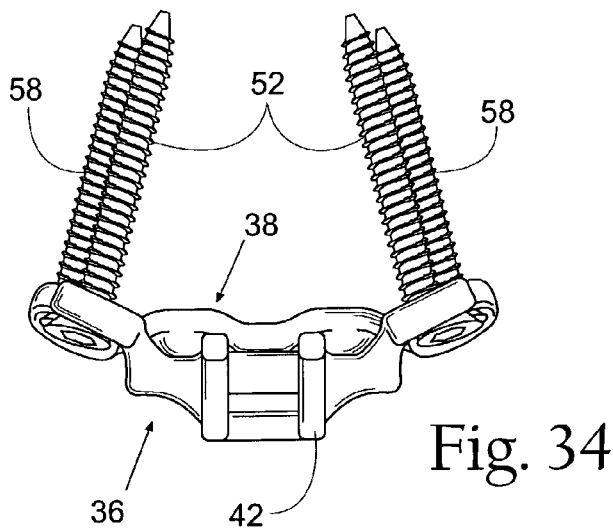
FIG. 34 is a top view of the articulated prostheses shown in FIG. 30.

As FIG. 28 best shows, the openings 56 are also oriented inward and downward. The inward orientation establishes a pre-defined pedicle entry angle for the fixation elements 58. The downward orientation of the fixation element 58 for the caudal prosthesis 38, in combination with the different, non-parallel orientation of the fixation element 52 for the cephalad prosthesis 36, establishes a desired lordotic angle.

B. Total Facet Replacement Using the Cephalad and Caudal Prostheses

With reference now principally to FIGS. 35 to 38, both the superior and inferior portions of the natural facet joint 32 are removed and replaced by the cephalad prosthesis 36 and the caudal prosthesis 38. More particularly, the inferior lamina 20 and the inferior portion of the natural facet joint 32 (e.g., the articulated inferior processes 28 and its supporting bone of the vertebral body 14 above the facet joint) is removed. The lamina may additionally be cut for a wide decompressive laminectomy along a decompressive superior-to-inferior resection line on one or both sides of the vertebral body.

The removed natural anatomy is replaced with the cephalad prosthesis 36. The superior portion of the natural facet joint 32 (e.g., the articulated superior process 26 and its supporting bone of the targeted vertebral body 14) is also removed. Desirably, the mamillary process, the accessory process, a portion of the transverse process, and a portion of the pedicle is removed by being rongeured or reamed. The removed natural anatomy is replaced with the caudal prosthesis 38.

Figure 35:
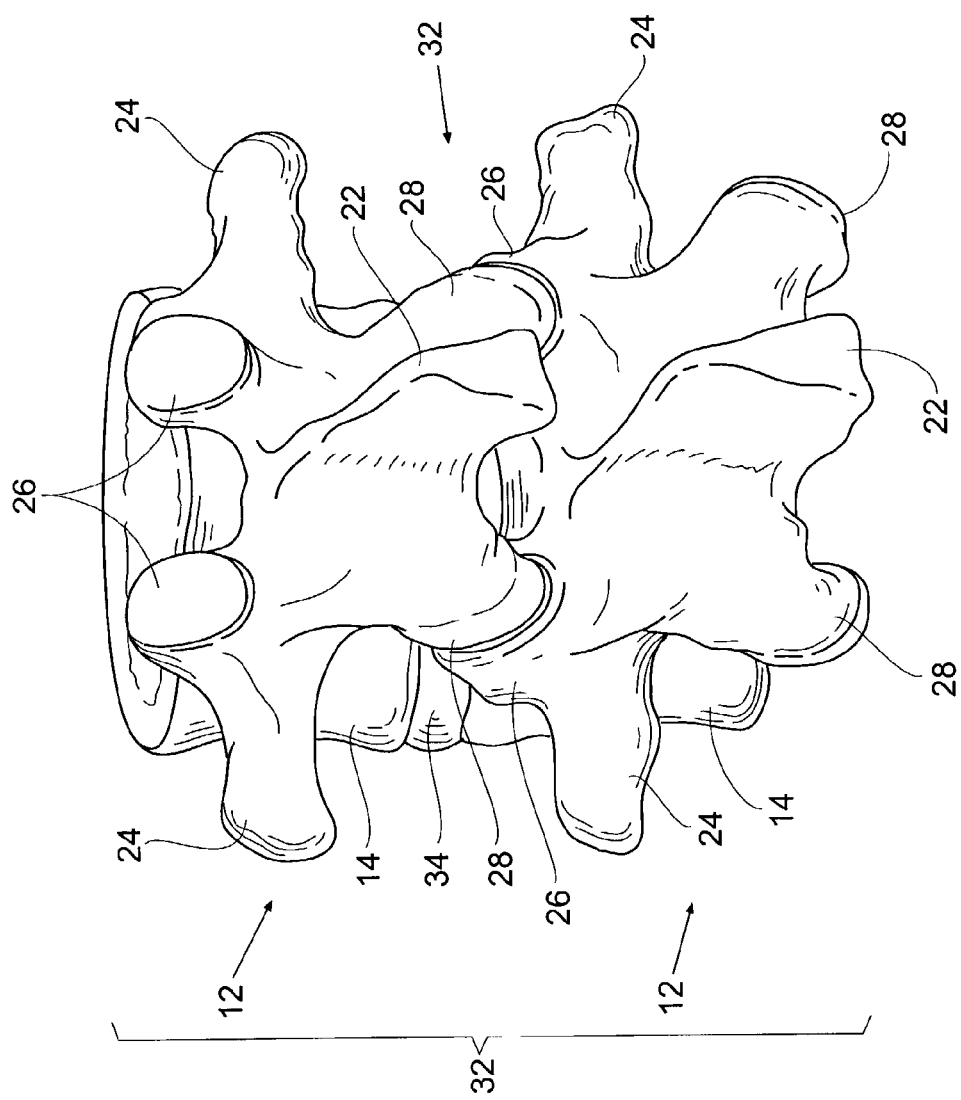
FIG. 35 is a posterior perspective view of the natural left and right facet joints between two lumbar vertebrae.

In one embodiment, a surgical procedure exposes the spinous process 22, lamina 20, and facet joints 32 at a desired level of the spine 10 using any method common to those of skill in the medical arts. FIG. 35 shows the exposed spinous process 22, lamina 20, and facet joint 32 of the L4-L5 joint.

The inferior portion of the facet joint 32 is cut at or near a selected resection line. Most of the lamina 20 is desirably preserved, as is the facet joint capsule, which may be opened and folded back. The facet joint capsule may be cut perpendicular to its direction. The natural inferior portion of the facet joint 32 may then be retracted from the superior portion. Once the inferior and superior portions of the facet joint are separated, the cut inferior bone, e.g., the inferior articular process 28 and its supporting bone, of the upper joint (e.g., the cut inferior portion of the L4 vertebra in the L4-L5 joint) may be removed, as depicted by phantom lines in FIG. 36. Alternatively, it may be possible to remove the cut inferior bone while simultaneously separating the facet joint 32.

Figure 36:
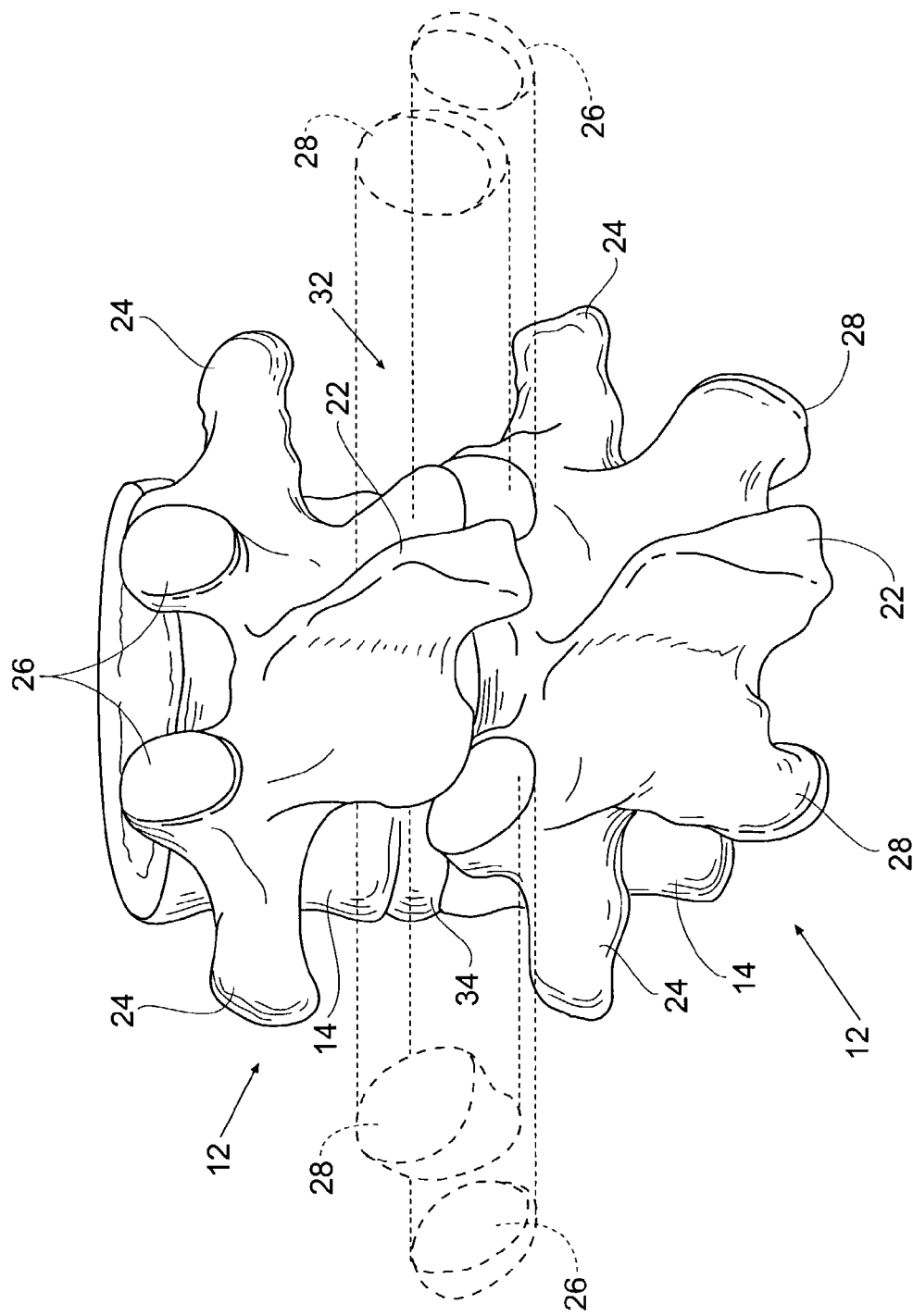
FIG. 36 is a posterior perspective view of the lumbar vertebrae shown in FIG. 35, showing the surgical removal of the natural inferior processes and related bony structure of the superior vertebra and the surgical removal of the natural superior processes and related bony structure of the inferior vertebra.

Prominent bone of the superior portion of the natural facet joint, e.g., the superior articular process 26 and its supporting bone, may be also removed, as depicted by phantom lines in FIG. 36, using any means common in the field. The superior portion of the natural facet joint 32 may also be trimmed to decompress the adjacent nerve root. A reamer or any other instrument that is useful for grinding or scraping bone, may be used to ream the superior portion of the facet joint 32 into the pedicle 16, to reach the geometry shown in FIG. 36, which is suitable for receiving the caudal prosthesis 38.

Figure 37:
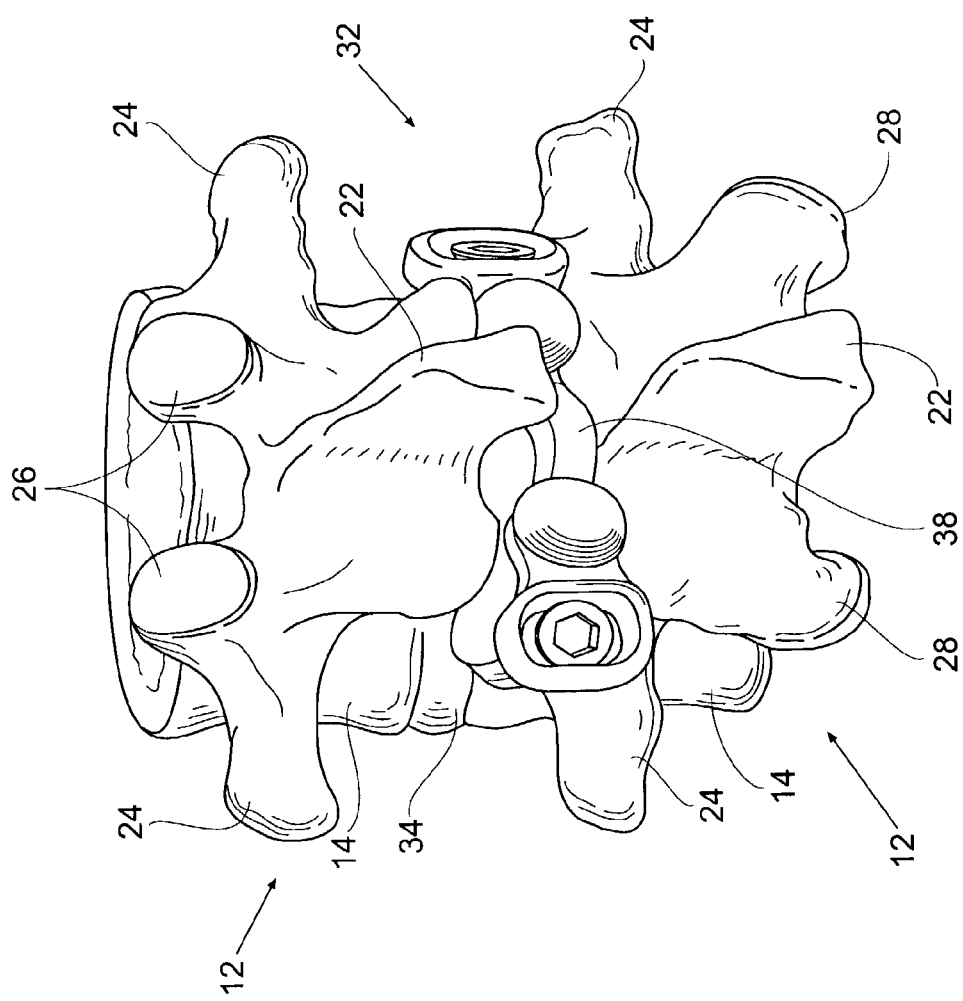
FIG. 37 is a posterior perspective view of the lumbar vertebrae shown in FIGS. 35 and 36, after removal of the inferior and superior halves of the natural facet joints, illustrating the fixation of a caudal prosthesis onto the inferior vertebra for replacing the superior halves of the natural facet joints that have been removed.

With reference to FIG. 37, the caudal prosthesis 38 as described above can be directly screwed or tapped into the vertebral body 14 using pedicle screws or other fixation elements 58.

Figure 38:
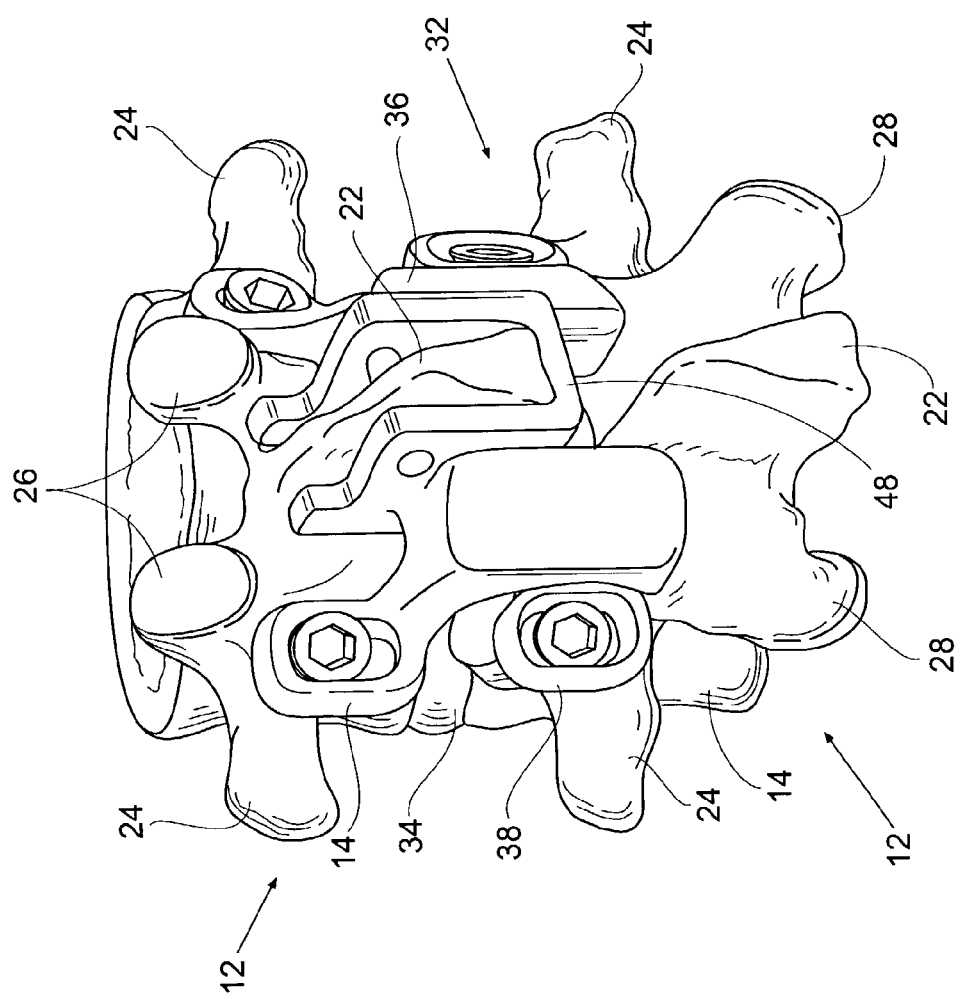
FIG. 38 is a posterior perspective view of the lumbar vertebrae shown in FIG. 37, after removal of the inferior and superior halves of the natural facet joints and the fixation of the caudal prosthesis onto the inferior vertebra, illustrating the fixation of a cephalad prosthesis on the superior vertebra for replacing the inferior halves of the natural facet joints that have been removed, the caudal and cephalad prostheses articulating to provide an artifical articulation that can be unlike the natural articulation of the removed natural facet joints.

With reference now to FIG. 38, the cephalad prosthesis 36, as described above, can be installed over the spinous process 22 and over the lamina 20, either before or after placement of the caudal prosthesis 38. The cephalad prosthesis 36 can be directly screwed or tapped using pedicle screws or other fixation elements 52 to the lamina 20 and to each pedicle 16. The cephalad prosthesis 36 can also be further attached to the spinous process 22 with a trans-spinous-process screw 48 to provide additional stability, as also previously described.

As shown in FIG. 38, articulation between the artificial facet joint structures 40/54 of the cephalad prosthesis and the caudal prosthesis 36 and 38 is established, to provide an artificial articular configuration in place of the preexisting natural articular configuration.

Because both the superior and inferior portions of the natural facet joint 32 and surrounding bone structures have been removed, the artificial facet joint structures 40/54 of the cephalad prosthesis 36 and the caudal prosthesis 38 can be installed in desired positions and orientations, free of anatomic constraints imposed by the preexisting articular configuration of either the inferior or superior portions of the natural facet joint 32. Furthermore, the artificial facet joint structures 40/54 of the cephalad prosthesis 36 and caudal prosthesis 38 can create an artificial articular configuration that is unlike the pre-existing natural articular configuration in terms of, e.g., interpedicle distance, lardotic angle, and contact stress, so that a desired articulation or bony anatomy can be totally restored. At the same time a desired bone anatomy is restored, decompression of the adjacent nerve root can be maintained to eliminate pain.

Further details of surgical procedures suitable for installing the prostheses are described in co-pending U.S. patent application Ser. No. 09/693,272, filed Oct. 20, 2000, and entitled "Facet Arthroplasty Devices and Methods," which is incorporated herein by reference.

The above described embodiments of this invention are merely descriptive of its principles and are not to be limited. The scope of this invention instead shall be determined from the scope of the following claims, including their equivalents.

What is claimed is:

1. A facet joint prosthesis to replace a portion of a natural facet joint connecting a first and second vertebral body, the prosthesis comprising
    a component sized to be fixed to the first vertebral body and including an artificial facet joint structure adapted to replace the portion of the natural facet joint and articulate with the second vertebral body,
    a fixation region on the component being configured and arranged to receive a fixation element to fix the component to the first vertebral body, the fixation region being sized to accommodate adjustment of the component on the first vertebral body.

2. A facet joint prosthesis according to claim 1 wherein the fixation region is sized to accommodate lateral adjustment of the component on the first vertebral body.

3. A facet joint prosthesis according to claim 1 wherein the fixation region is sized to accommodate inferior-superior adjustment of the component on the vertebral body.

4. A facet joint prosthesis according to claim 1 wherein the artificial facet joint structure comprises a generally convex articulating surface.

5. A facet joint prosthesis according to claim 1 wherein the artificial facet joint structure comprises a generally concave articulating surface.

6. A facet joint prosthesis according to claim 1 wherein the artificial facet joint structure comprises a surface adapted to articulate with a facet structure of the second vertebra.

7. A facet joint prosthesis according to claim 1 wherein the artificial facet joint structure comprises a surface adapted to articulate with an artificial facet structure on the second vertebra.

8. A facet joint prosthesis according to claim 1 wherein the artificial facet joint structure is adapted to replace a cephalad portion of the natural facet joint.

9. A facet joint prosthesis according to claim 1 wherein the artificial facet joint structure is adapted to replace a caudal portion of the natural facet joint.

10. A facet joint prosthesis according to claim 1 wherein the fixation region is configured and arranged to support the fixation element at a desired entry angle.

11. A facet joint prosthesis according to claim 1 wherein the fixation region is configured and arranged to support the fixation element at an angle that approximates a desired lordotic angle.

12. A facet joint prosthesis according to claim 1 further including a second fixation region on the component being configured and arranged to fix the component to the first vertebral body on or near a spinous process.

13. A facet joint prosthesis to replace, on a vertebral body, a portion of a natural facet joint, the prosthesis comprising
    a component sized to be fixed to the vertebral body and including an artificial facet joint structure adapted to replace the portion of the natural facet joint, the artificial facet joint structure being mounted for movement on the component.

14. A facet joint prosthesis according to claim 13 wherein the artificial facet joint structure is mounted for posterior-anterior movement on the component.

15. A facet joint prosthesis according to claim 13 wherein the artificial facet joint structure comprises a generally convex surface.

16. A facet joint prosthesis according to claim 13 wherein the artificial facet joint structure comprises a generally concave surface.

17. A facet joint prosthesis according to claim 13 wherein the artificial facet joint structure comprises a surface adapted to articulate with another facet joint structure.

18. A facet joint prosthesis according to claim 13 wherein the artificial facet joint structure comprises a surface adapted to articulate with another artificial facet joint structure.

19. A facet joint prosthesis according to claim 13 wherein the artificial facet joint structure is adapted to replace a cephalad portion of the natural facet joint.

20. A facet joint prosthesis according to claim 13 wherein the fixation region is configured and arranged to support the fixation element at a desired pedicle entry angle.

21. A facet joint prosthesis according to claim 13 wherein the fixation region is configured and arranged to support the fixation element at an angle that approximates a desired lordotic angle.

22. A facet joint prosthesis according to claim 13 further including a second fixation region on the component being configured and arranged to fix the component to the vertebral body on or near a spinous process.

23. A prosthesis assembly for replacing a first portion and a second portion of a natural facet joint comprising
    a cephalad prosthesis comprising a first component sized to be fixed to a first vertebral body and including a first artificial joint structure adapted to replace the first portion of the natural facet joint, a first fixation region on the first component being configured and arranged to receive a first fixation element to fix the first component to the first vertebral body, the first component further including a first articulating surface,
    a caudal prosthesis comprising a second component sized to be fixed to a second vertebral body and including a second artificial joint structure adapted to replace the second half of the natural facet joint, a second fixation region on the second component being configured and arranged to receive a second fixation element to fix the second component to the second vertebral body, the second component further including a second articulating surface,
    the first and second articulating surfaces interacting to allow the first and second vertebral bodies to articulate relative to each other, and
    at least one of the first and second fixation regions being sized to accommodate adjustment of the respective first or second components on the respective first or second vertebral body.

24. A prosthesis assembly according to claim 23 wherein the at least one of the first or second fixation regions is sized to accommodate lateral adjustment of the respective first or second component on the respective first or second vertebral body.

25. A prosthesis assembly according to claim 23 wherein the at least one fixation region is sized to accommodate inferior-superior adjustment of the respective component on the respective vertebral body.

26. A prosthesis assembly according to claim 23 wherein the first artificial joint structure comprises a generally convex surface, and wherein the second artificial joint structure comprises a generally concave surface articulating with the generally convex surface.

27. A prosthesis assembly according to claim 23 wherein the first artificial joint structure comprises a generally concave surface, and wherein the second artificial joint structure comprises a generally convex surface articulating with the generally concave surface.

28. A prosthesis assembly according to claim 23 wherein the first and second artificial joint structures comprise articulating metal surfaces having a contact stress less than about 25,000 psi when the prosthesis assembly is experiencing a normal physiological load.

29. A prosthesis assembly according to claim 28 wherein the contact stress is less than about 12,000 psi.

30. A prosthesis assembly according to claim 23 wherein at least one of the first and second artificial joint structures comprises an articulating polymer surface having a contact stress less than about 10,000 psi when the prostheses assembly is undergoing normal physiological loading.

31. A prosthesis assembly according to claim 30 wherein the contact stress is less than about 5,000 psi.

32. A prosthesis assembly according to claim 23 wherein at least one of the first and second fixation regions is configured and arranged to support the respective fixation element at a desired entry angle.

33. A prosthesis assembly according to claim 23 wherein at least one of the first and second fixation regions is configured and arranged to support the respective fixation element at an angle that approximates a desired lordotic angle.

34. A prosthesis assembly according to claim 23 wherein the respective cephalad or caudal prosthesis further includes an auxiliary fixation region on the respective first or second component configured and arranged to fix the respective first or second component to the respective first or second vertebral body on or near a spinous process.

35. A prosthesis assembly according to claim 23 wherein the first artificial facet joint structure is mounted for movement on the cephalad prosthesis.

36. A prosthesis assembly for replacing the cephalad and caudal portions of a natural facet joint comprising
a cephalad prosthesis comprising a first component sized to be fixed to a first vertebral body and including a first artificial facet joint structure adapted to replace the cephalad portion of the natural facet joint,
a caudal prosthesis comprising a second component sized to be fixed to a second vertebral body and including a second artificial facet joint structure adapted to replace the caudal portion of the natural facet joint,
the first and second artificial facet joint structures articulating to allow the first vertebral body to move relative to the second vertebral body, and
the first and second artificial facet joint structures comprise articulating metal surfaces having a contact stress less than about 25,000 psi when the first and second vertebral bodies are undergoing normal physiological loading.

37. A prosthesis assembly according to claim 36 wherein the contact stress is less than about 12,000 psi.

38. A prosthesis assembly for replacing the cephalad and caudal portions of a natural facet joint comprising
a cephalad prosthesis comprising a first component sized to be fixed to a vertebral body and including a first artificial facet joint structure adapted to replace the cephalad portion of the natural facet joint,
a caudal prosthesis comprising a second component sized to be fixed to a second vertebral body and including a second artificial facet joint structure adapted to replace the caudal portion of the natural facet joint, the first and second artificial facet joint structures articulating to allow the first vertebral body to move relative to the second vertebral body, and
at least one of the first and second artificial facet joint structures comprises an articulating polymer surface having a contact stress less than about 10,000 psi when the first and second vertebral bodies are undergoing normal physiological loading.

39. A prosthesis assembly according to claim 38 wherein the contact stress is less than about 5,000 psi.

40. A facet joint prosthesis to replace a portion of a natural facet joint connecting a first and a second vertebral body, the prosthesis comprising
a component sized to be fixed to the vertebral body and including an artificial joint structure adapted to replace the portion of the natural facet joint and articulate with the second vertebral body, a fixation element on the component being configured and arranged to engage a portion of the lamina to fix the component to the first vertebral body.

41. A facet joint prosthesis according to claim 40 wherein the fixation element comprises a hook.

42. A facet joint prosthesis to replace a portion of a natural facet joint connecting a first and second vertebral body, the prosthesis comprising
a component sized to be fixed to the first vertebral body and including an artificial joint structure adapted to replace the portion of the natural facet joint and articulate with the second vertebral body,
a fixation region on the component being configured and arranged to receive a fixation element to fix the component to the first vertebral body, the fixation region being configured and arranged to support the fixation element at a desired entry angle.

43. A facet joint prosthesis according to claim 42 wherein the component includes laterally spaced first and second fixation regions each being configured and arranged to support a fixation element at a desired entry angle.

44. A facet joint prosthesis according to claim 43 wherein the desired pedicle entry angle for the first fixation region differs from the desired pedicle entry region for the second fixation region.

45. A facet joint prosthesis according to claim 42 wherein the fixation region is configured and arranged to support the fixation element at an angle that approximates a desired lordotic angle.

46. A facet joint prosthesis to replace a portion of a natural facet joint, the prosthesis comprising
a component sized to be fixed to the first vertebral body and including an artificial joint structure adapted to replace the portion of the natural facet joint and articulate with another facet joint prosthesis or a natural facet prosthesis, a fixation region on the component being configured and arranged to receive a fixation element to fix the component to the first vertebral body, the fixation region being configured and arranged to support the fixation element at an angle that approximates a desired lordotic angle.

47. A method of replacing, on a vertebral body, a portion of a natural facet joint using the prosthesis as defined in claim 1, the method comprising the steps of (i) removing at least a portion of the natural facet joint from the vertebral body, and (ii) fixing the prosthesis as defined in claim 1 to the vertebral body to replace the removed portion of the natural facet joint with the artificial facet joint structure.

48. A method of replacing, on a vertebral body, a portion of a natural facet joint using the prosthesis as defined in claim 13, the method comprising the steps of (i) removing at least a portion of the natural facet joint from the vertebral body, and (ii) fixing the prosthesis as defined in claim 13 to the vertebral body to replace the removed portion of the natural facet joint with the artificial facet joint structure.

49. A method for replacing the inferior and superior halves of a natural facet joint comprising the steps of
  removing the inferior and superior halves of the natural facet joint,
  fixing a cephalad prosthesis to a vertebral body that includes a first artificial facet joint structure to replace the inferior half of the natural facet joint,
  fixing a caudal prosthesis to a vertebral body that includes a second artificial facet joint structure to replace the superior half of the natural facet joint, the first and second artificial facet joint structures articulating to form, respectively, the superior and inferior halves of an artificial facet joint, and
  selecting for the first and second artificial facet joint structures articulating metal surfaces having a contact stress less than about 25,000 psi.

50. A method according to claim 49 wherein the contact stress is less than about 12,000 psi.

51. A method for replacing the inferior and superior halves of a natural facet joint comprising the steps of
  removing the inferior and superior halves of the natural facet joint;
  fixing a cephalad prosthesis to a vertebral body that includes a first artificial facet joint structure to replace the inferior half of the natural facet joint;
  fixing a caudal prosthesis to a vertebral body that includes a second artificial facet joint structure to replace the superior half of the natural facet joint, the first and second artificial facet joint structures articulating to form, respectively, the superior and inferior halves of an artificial facet joint; and
  selecting for the first and second artificial facet joint structures at least one articulating polymer surface having a contact stress less than about 10,000 psi.

52. A method according to claim 51 wherein the contact stress is less than about 5,000 psi.

53. A method of replacing, on a vertebral body, a portion of a natural facet joint using the prosthesis as defined in claim 40, the method comprising the steps of
  (i) removing at least a portion of the natural facet joint from the vertebral body, and
  (ii) fixing the prosthesis as defined in claim 40 to the vertebral body to replace the removed portion of the natural facet joint with the artificial joint structure.

54. A method of replacing, on a vertebral body, a portion of a natural facet joint using the prosthesis as defined in claim 42, the method comprising the steps of
  (i) removing at least a portion of the natural facet joint from the vertebral body, and
  (ii) fixing the prosthesis as defined in claim 42 to the vertebral body to replace the removed portion of the natural facet joint with the artificial joint structure.

55. A method of replacing, on a vertebral body, a portion of a natural facet joint using the prosthesis as defined in claim 46, the method comprising the steps of
  (i) removing at least a portion of the natural facet joint from the vertebral body, and
  (ii) fixing the prosthesis as defined in claim 46 to the vertebral body to replace the removed portion of the natural facet joint with the artificial joint structure.

* * * * *